United States Patent [19]
Eilon et al.

[11] Patent Number: 5,733,911
[45] Date of Patent: Mar. 31, 1998

[54] METHOD FOR INDUCING DEATH OF NEOPLASTIC CELLS USING PIPERAZNE DERIVATIVES

[75] Inventors: Gabriel F. Eilon, Long Beach; John W. Jacobs, Irvine, both of Calif.

[73] Assignees: Hitachi Chemical Co., Ltd., Tokyo, Japan; Hitachi Chemical Research Center, Inc., Irvine, Calif.; Nippon Chemiphar Co., Ltd., Tokyo, Japan

[21] Appl. No.: 592,540

[22] Filed: Jan. 26, 1996

[51] Int. Cl.$^6$ .......................... A61K 31/495; A61K 31/50
[52] U.S. Cl. ............................................................. 514/252
[58] Field of Search ................................................ 514/252

[56] References Cited

U.S. PATENT DOCUMENTS

| | | |
|---|---|---|
| 4,333,879 | 6/1982 | Tamai et al. |
| 4,382,889 | 5/1983 | Tamai et al. |
| 4,418,075 | 11/1983 | Tamai et al. |
| 4,474,800 | 10/1984 | Tamai et al. |
| 4,507,297 | 3/1985 | Masaki et al. |
| 4,596,803 | 6/1986 | Masaki et al. |
| 4,732,910 | 3/1988 | Yaginuma et al. |
| 5,214,056 | 5/1993 | Haruta et al. ............ 514/326 |
| 5,336,783 | 8/1994 | Omura et al. |
| 5,422,359 | 6/1995 | Ando et al. |

FOREIGN PATENT DOCUMENTS

PCT/US93/
06143   6/1993   WIPO.

OTHER PUBLICATIONS

Kamiya Biomedical Co., catalogue, winter, 1995.
Cell Biology, vol. 63, pp. 146–150, Jan. 1988, Yoko Shoji–Kasai, Mitsuko Senshu, Shintaro Iwashita and Kazutomo Imahori.
Science vol. 267, pp. 1456–1462, Mar. 10, 1995, Craig B. Thompson.
Biochemical and Biophysical Research Communication vol. 214, No. 3, pp. 1130–1137, Sep. 25, 1995, Wen Zhu, Patricia E. Murtha and Charles Y. F. Yong.
Histol Histopathol (Spain), 9 (3) P485–493, ISSN 0213–3911, Jul. 1994, Logothetou–Rella.
Abstract, Piperazine derivatives as oral thiol protease inhibitors, Japanese Patent No. JP63275575, Mitsuo Mazaki, et al. (1987).

*Primary Examiner*—Jerome D. Goldberg
*Attorney, Agent, or Firm*—Knobbe, Martens, Olson & Bear, LLP

[57] ABSTRACT

A method for inducing cell death in neoplastic cells, includes the step of administering a compound of formula I or a pharmaceutically acceptable salt thereof, as a primary chemotherapeutic agent or substantially contemporaneously with chemotherapy, to a patient having multidrug-resistant neoplastic cells, in an amount sufficient to induce cell death in the neoplastic cells:

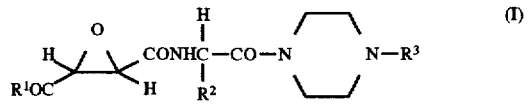

where $R^1$ is hydroxyl, C1–4 alkoxyl, C1–4 alkylcarboxyloxymethoxyl, phenyl C1–2 alkylamino group, 2,5-pyrrolidinedione-1-alkoxyl (C1–4), or

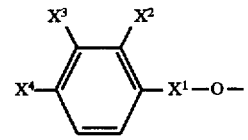

wherein $X^1$ is a chemical bond or C1–2 alkylene, $X^2$ is hydrogen or carboxyl forming a 5-membered ring with $X^1$ when $X^2$ is methylene, $X^3$ is hydrogen or C1–2 alkyl, $X^4$ is hydrogen or C1–2 alkyl, or $X^3$ and $X^4$ together form a 5-membered ring, in which at least one of $X^2$, $X^3$, and $X^4$ is hydrogen, $R^2$ is C3–4 alkyl, $R^3$ is C1–4 alkyl,

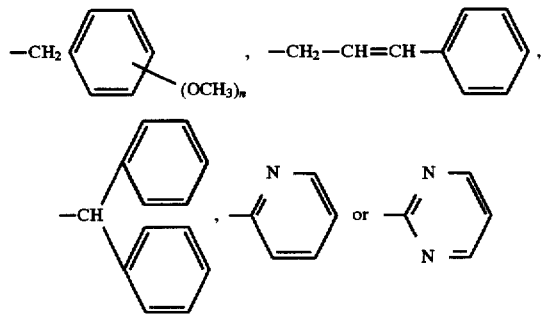

in which n is an integer of 0 to 3.

14 Claims, 37 Drawing Sheets

METHOD FOR INDUCING DEATH OF NEOPLASTIC CELLS USING PIPERAZNE DERIVATIVES

BACKGROUND

1. Field of the Invention

This invention relates to a method for inducing death of neoplastic cells and potentiating chemotherapy to treat neoplastic cells, and particularly to such a method for activating programmed cell death of neoplastic cells and reversing multidrug resistance in neoplastic cells, using piperazine derivatives.

2. Background of the Art

Certain epoxide compounds are known as pharmacologically active compounds in a variety of pharmaceutical fields, including in the field of cancer treatment. Numerous epoxide compounds have been synthesized for various purposes. For example, U.S. Pat. Nos. 4,507,297 and 4,596,803 to Masaki et al. disclose piperazine derivatives having an epoxide group including NCO-700 used for the purpose of inhibiting myocardial infarction. U.S. Pat. No. 5,336,783 to Omura et al. discloses a pyrrole derivative having a carbamoyl group, which has calpain inhibitory activity. U.S. Pat. No. 4,732,910 to Yaginuma et al. discloses an epoxide compound having a guanidino group and a benzyl group, which has strong enzyme inhibitory activity against thiol proteases. U.S. Pat. Nos. 4,333,879 and 4,382,889 to Tamai et al. disclose EST as a compound having thiol protease inhibitory activity, especially calcium-activated neutral protease (CANP) inhibitory activity. U.S. Pat. Nos. 4,418,075 and 4,474,800 to Tamai et al. disclose compounds having a similar chemical structure to that of EST, but which contains one more imino group than EST does.

The compounds described in the preceding paragraph have thiol protease inhibitory activity, especially against CANP (also known as calpain). However, none of the above compounds, have been reported as effective in the direct treatment of cancer cells, despite the fact that calpain inhibitors have some pharmaceutical effects on humans.

A number of other calpain inhibitors have been disclosed for various utilities. For Example, U.S. Pat. No. 5,403,834 to Malfroy-Camine et al. discloses salen-transition metal complexes which have potent antioxidant and/or free radical scavenging properties. The compounds are said to prevent or reduce ischemic/reperfusion damage to critical tissues such as the myocardium and central nervous system. U.S. Pat. No. 5,328,922 to Nixon, et al. discloses two related endogenous neural, especially human brain, calcium-activated neutral protease (CANP or calpain) inhibitors which are known as high molecular weight calpastatin (HMWC) and low molecular weight calpastatin (LMWC). U.S. Pat. No. 5,268,164 to Kozarich, et al. discloses peptides (permeabilizer A-7) having a core sequence of amino acids or amino acid analogues which increase the permeability of the blood-brain barrier in an animal. U.S. Pat. Nos. 5,424, 325, 5,422,359, 5,416,117, 5,395,958, and 5,340,909 to Ando et al. disclose aminoketone derivatives ('325), alpha-aminoketone derivatives ('359), and cyclopropenone derivatives ('117, '958, and '909), which are reversible inhibitors against thiol proteases, such as calpain. These compounds are said to have excellent properties in tissue distribution, cell membrane permeability, and absorption on oral administration. Treatment of cancer cells is not mentioned in connection with the compounds.

International Application Publication No. WO 94/00095 discloses the use of various calpain inhibitors in order to synchronize the cell cycle. The synchronization is disclosed to shorten the duration of chemotherapy for cancer and to increase the activity of chemotherapeutic agents. The rationale is that synchronization of all cells in the S phase will render them more sensitive to the chemotherapeutic agents. This reference teaches that, in the use of calpain inhibitors in the treatment of cancer, calpain inhibitors must be used prior to treatment of cancer with a primary chemotherapeutic agent. Further, there is no disclosure or suggestion of treatment of cancer cells which have multidrug resistance. Moreover, in no way is there any disclosure or suggestion of administering the calpain inhibitors by themselves to induce cell death in cancer, i.e., the calpain inhibitors are not disclosed to have a beneficial effect unless they are administered prior to treatment of cancer with a primary chemotherapeutic agent.

Shoji-Kasai et al. *Proc. Natl. Acad. Sci., USA* 85:146–150 (1988) shows that epidermoid carcinoma A431 cells cultured in a chemically defined medium can be arrested at mitotic metaphase by E-64-d which is a membrane-permeant derivative of the thiol protease-specific inhibitor E-64. This reference shows that inhibitors of CANP appear to have significant effects in slowing the growth of certain cancers. However, the effects will not be exhibited when cancer cells have multidrug resistance, and will not lead to cell death in cancer.

A major factor limiting the clinical usefulness of anticancer drugs is the development of drug resistance in tumors. Many tumors which are treated with anticancer drugs such as vinca alkaloids (vinblastine) and antracyclines (doxorubicin) develop tolerance to these drugs and also show cross-resistance to other cancer drugs as well. In some cases, patients do not respond to initial chemotherapy at all, and in these cases it is thought that the neoplasms have intrinsic drug-resistance. One of the mechanisms of this drug resistance is thought to reside in the active pumping of cancer drugs out of the cancer cell by a surface protein called the mdr (multiple drug resistance) protein (Gottesman et al., *J Clinical Oncology* 7:409–411, 1989, Goldstein et al., *J Nat'l Cancer Inst.* 81: 116–124, 1989, Fojo et al., *Cancer Res.* 45:3002–3007, 1985). This protein effectively lowers the concentration of anticancer drugs within the cancer cell leading to survival and growth of the tumor. The mdr protein has been characterized as a 170,000 dalton, energy-dependent glycoprotein, which becomes highly amplified in cancer cells as they acquire drug resistance. The pump is thought to recognize and efflux a number of hydrophobic drugs and its normal role in the body is thought to be as a pump which can recognize and rid cells of potentially toxic compounds.

A number of chemical compounds have been reported to block the activity of the mdr pump allowing anticancer drugs to accumulate in the target cells. These compounds are thought to work by acting as substrates for the multidrug pump system, and by overwhelming the pump to prevent the efflux of cancer drugs resulting in cancer cell death. The most intensely studied of these mdr-blocking compounds has been verapamil, a calcium-channel blocker which has a different clinical use, namely the treatment of hypertension. In both preclinical and clinical studies (Gottesman et al., *J Clinical Oncology* 7:40–411, 1989), verapamil has shown good activity in inhibiting the mdr pump, resulting in enhanced killing of cancer cells. Unfortunately, the doses of verapamil needed to inhibit the pump are so high that toxic cardiovascular side effects were seen in patients, thus preventing the further development of this drug for use in cancer patients. Nevertheless, the development of nontoxic agents that can reverse the mdr pump are needed and would be an important addition to the treatment of cancer patients. As shown in Table 1 below, the number of cancer patients in the United States who develop drug resistance is approximately 30% and, thus, the market for safe, effective blockers of mdr pump is significant.

TABLE 1

Drug Resistance in U.S. Cancer Patients[1]

| | |
|---|---|
| Number of Cancer Patients (U.S.) | 1,200,000 |
| Number of New Patients/Year | 900,000 |
| Estimated Number of Patients with Drug-Resistant Cancer | 350,000 |

[1]Numbers quoted from *BioTechnology News* and *Journal of the National Cancer Institute*

With regard to treatment of multidrug resistant cancer cells, U.S. Pat. No. 5,371,081 discloses N-substituted phenoxazines. These compounds are chemically unrelated to the above-discussed epoxide compounds and calpain inhibitors. Further, the compounds are not disclosed to be beneficial when administered by themselves, and the toxicity of the compounds are likely to be an obstacle to clinical use.

One of the most serious problems residing in conventional chemotherapy is the toxicity of chemotheraputic agents. For example, vinblastine and adriamycin, typifying chemotheraputic agents, have inevitable side effects such as hair loss, weight loss, and liver and kidney damage. They cannot be administered daily for a long period of time due to high toxicity. For example, these chemotherapeutic agents are normally administered several days a week for two or three months, and after several weeks of recuperation without administration of the chemotherapeutic agents, the administration thereof is repeated. None of the conventional chemotherapeutic agents and potentiators is free of toxicity.

In conclusion, no prior art discloses or suggests calpain inhibitory compounds or epoxide compounds which themselves are practically capable of inducing cell death in cancer. Moreover, there is no disclosure of compounds which function to kill cancer cells, irrespective of the existence of multidrug resistance in the cancer cells, without significant side effects or toxicity.

SUMMARY OF THE INVENTION

The present invention has exploited use of epoxide derivatives in the treatment of cancer, and in particular, in order to treat cancer cells, irrespective of the existence of multidrug resistance in the cancer cells, use of piperazine derivatives having epoxy groups as a primary chemotherapeutic agent or as adjunctive therapy when used substantially contemporaneously with other chemotherapeutic agents. An objective of the present invention is to provide a method for significant induction of cell death in cancer, using piperazine derivatives having epoxy groups, which is pharmacologically beyond prevention of metastasis in cancer or the like mentioned in the prior art. Another objective of the present invention is to provide a method for significant induction of cell death in cancer, using piperazine derivatives having epoxy groups alone or as a primary chemotherapeutic agent. In other words, the piperazine derivatives themselves function as an anticancer drug, irrespective of the existence of multidrug resistance in the cancer cells, based on a mechanism different from that of conventional anticancer drugs. Still another objective of the present invention is to provide a method for reversal of multidrug resistance in cancer cells by using piperazine derivatives having epoxy groups as adjunctive therapy when used substantially contemporaneously with other chemotherapeutic agents.

Namely, one important aspect of the present invention is a method for inducing cell death in neoplastic cells, comprising: administering a compound of formula I or a pharmaceutically acceptable salt thereof, to a patient having neoplastic cells, in an amount sufficient to induce cell death in said neoplastic cells:

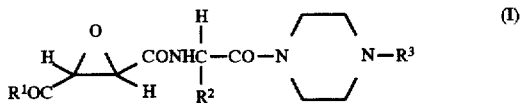

where $R^1$ is hydroxyl, C1–4 alkoxyl, C1–4 alkylcarbonyloxymethoxyl, phenyl C1–2 alkylamino group, 2,5-pyrrolidinedione-1-alkoxyl (C1–4), or

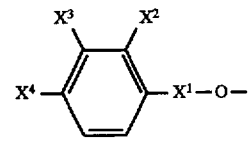

wherein $X^1$ is a chemical bond or C1–2 alkylene, $X^2$ is hydrogen or carboxyl forming a 5-membered ring with $X^1$ when $X^1$ is methylene, $X^3$ is hydrogen or C1–2 alkyl, $X^4$ is hydrogen or C1–2 alkyl, or $X^3$ and $X^4$ together form a 5-membered ring, in which at least one of $X^2$, $X^3$, and $X^4$ is hydrogen, $R^2$ is C3–4 alkyl, $R^3$ is C1–4 alkyl,

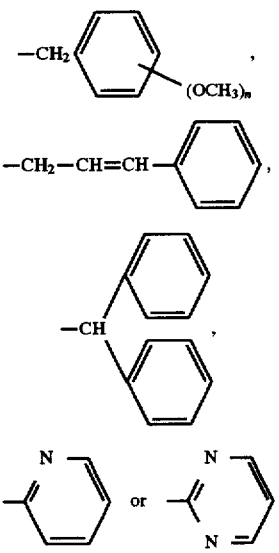

in which n is an integer of 0 to 3.

In the above method, the compound is preferably of the following formula:

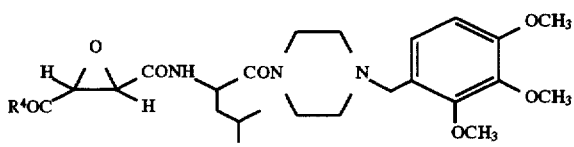

where R⁴ is selected from the group consisting of:

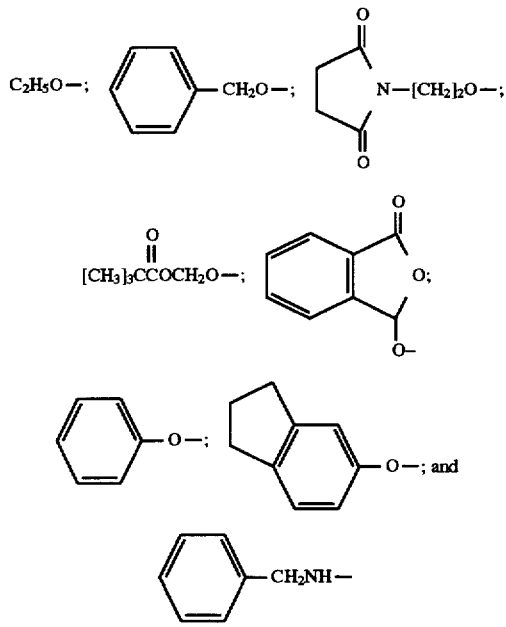

Also, in the above method, the compound is preferably of the following formula:

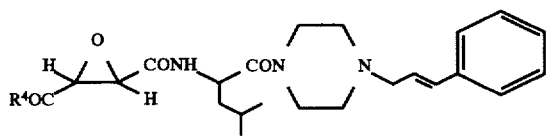

where R⁴ is selected from the group consisting of:

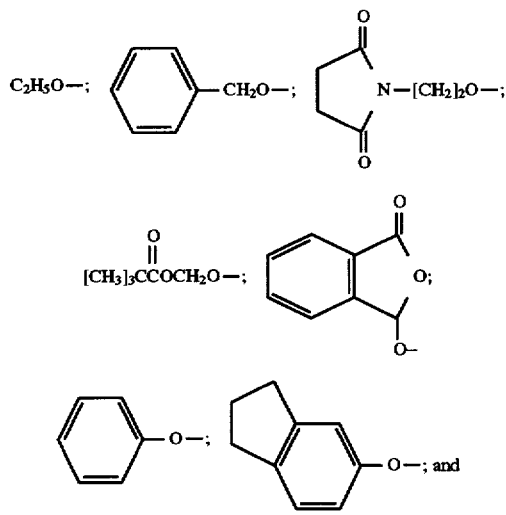

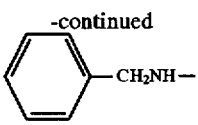

The above compounds are effective in inducing cell death in cancer, even when the cancer cells have multidrug resistance. The compounds are preferably in the form of sulfate.

The above compounds include the piperazine derivatives disclosed in U.S. Pat. Nos. 4,507,297 and 4,596,803 to Masaki et al, and Japanese Patent Laid-open Nos. 63-275575 (1988) and 63-275576 (1988). These patents are hereby incorporated herein by reference. However, the piperazine derivatives in '297 and '803 have been reported only for the purpose of inhibiting myocardial infarction. The above particular group of piperazine derivatives exhibits surprisingly and unexpectedly high anti-neoplastic activity on neoplasms, especially on those having multidrug resistance. The neoplasms which can be effectively treated are selected from the group consisting of human breast cancer cells, human melanoma cells, human ovarian cancer cells, human colon cancer cells, human pancreatic cancer cells, and human prostate cancer cells, particularly undifferentiated cancer cells.

Another important aspect of the present invention is a method for treating neoplastic cells, consisting essentially of administering a composition consisting essentially of a compound of formula I indicated earlier or a pharmaceutically acceptable salt thereof to a patient having multidrug-resistant neoplastic cells, in an amount sufficient to induce cell death in said neoplastic cells. The preferred compounds and the effective neoplasms described earlier can be adopted in the above method. The piperazine derivatives themselves in the present invention demonstrate significantly high anti-neoplastic activity on cancer cells, even when no other chemotherapeutic agents are used. This unexpected finding appears to be based on "apoptosis", i.e., programmed cell death which only recently has been recognized (Desoize B., Anticancer Res. 14:221–2294, 1994), in addition to the reversal of multidrug resistance expressed by an active mdr gene. The significant induction of cell death in cancer, via its apoptosis and reversal of multidrug resistance, by the piperazine derivatives in the present invention is pharmacologically very different from and beyond, for example, the reported prevention of metastasis in cancer by thiol protease-specific inhibitor E-64-d which has an epoxy group but no piperazine ring (Shoji-Kasai et al. Proc. Natl. Acad. Sci., USA 85:146–150, 1988). Further, the use of the piperazine derivatives in the present invention as a primary chemotherapeutic agent or as adjunctive therapy when used substantially contemporaneously with other chemotherapeutic agents is very distinct from the reported use of calpain inhibitors which must be used prior to treatment for cancer with a primary chemotherapeutic agent (International Application Publication No. WO 94/00095).

The above piperazine derivatives are also effective in conjunction with the use of a chemotherapeutic agent such as vinblastine and adriamycin by administering the piperazine derivatives substantially contemporaneously with the chemotherapeutic agent to a patient having neoplastic cells, particularly those carrying an active mdr gene.

Thus, another important aspect of the present invention is a method for potentiating chemotherapy to treat neoplastic cells, comprising administering a compound of formula I indicated earlier or a pharmaceutically acceptable salt thereof to a patient having multidrug-resistant neoplastic cells, substantially contemporaneously with chemotherapy, in an amount sufficient to potentiate said chemotherapy. The preferred compounds and the effective neoplasms described earlier can be adopted in the above method. The piperazine derivatives in the present invention are highly effective in reversing drug resistance in human cancer cells and tumors that are resistant to anticancer drugs, via highly accumulating the anticancer drugs in these cancer cells, thereby increasing the killing of these cancer cells.

BRIEF DESCRIPTION OF THE DRAWINGS

FIG. 36 is graphs showing the results of apoptosis activity of TOP-008 in apoptosis detection assays of human cancer cell line HS-578T.

DETAILED DESCRIPTION OF THE PREFERRED EMBODIMENTS

Figure 1:
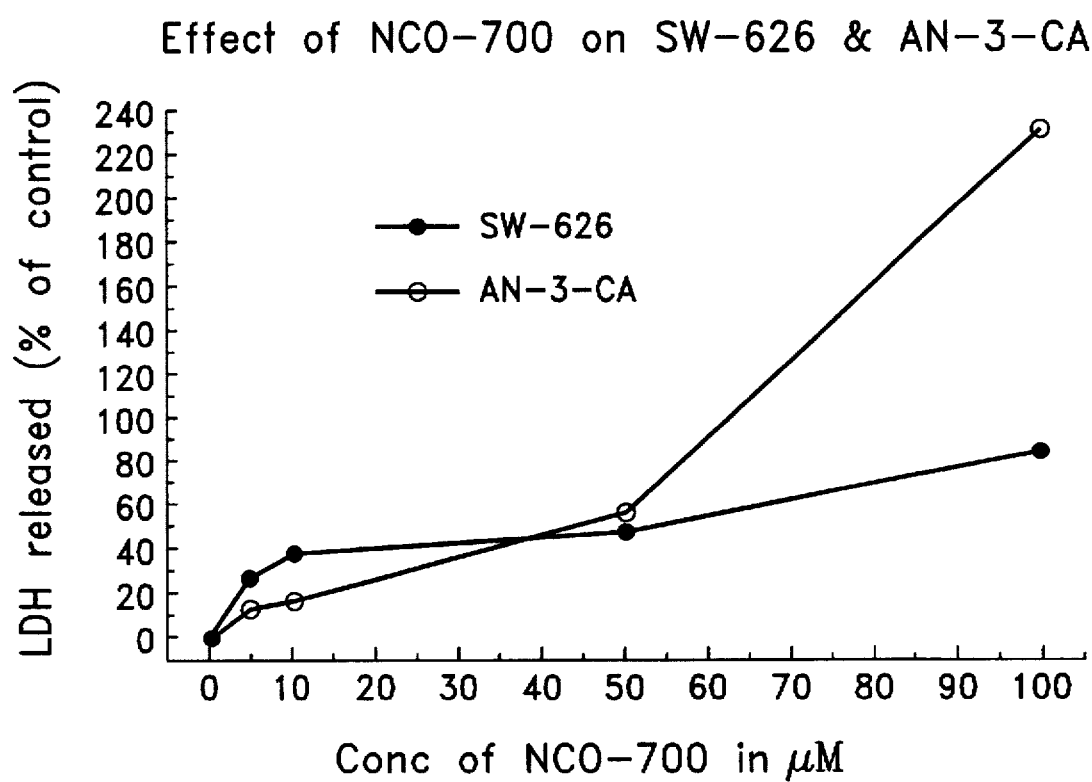
FIG. 1 is a graph showing the relationship between LDH released and the concentration of NCO-700 in cancer cell death assays of human ovarian cancer cell lines SW-626 and AN-3-CA.
Figure 2:
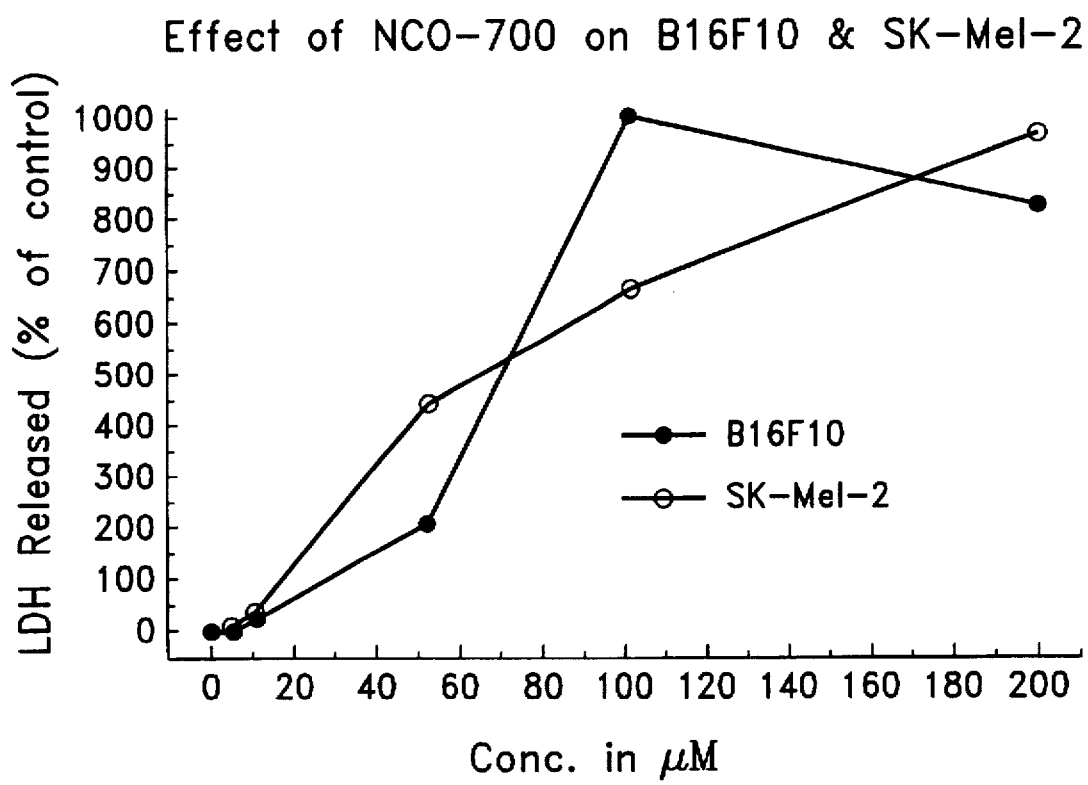
FIG. 2 is a graph showing the relationship between LDH released and the concentration of NCO-700 in cancer cell death assays of melanoma cell lines B16F10 (mouse line) and SK-Mel-2 (human line).
Figure 3:
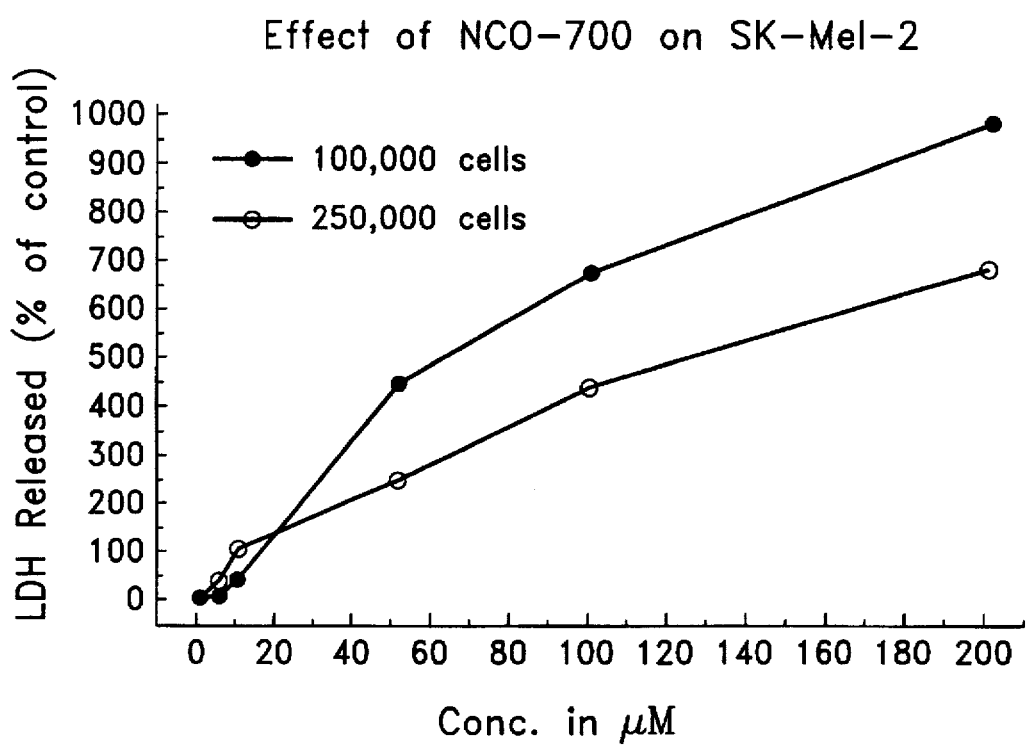
FIG. 3 is a graph showing the relationship between LDH released and the concentration of NCO-700 in cancer cell death assays of human cell line SK-Mel-2 (melanoma) of 100,000 cells and 250,000 cells.
Figure 4:
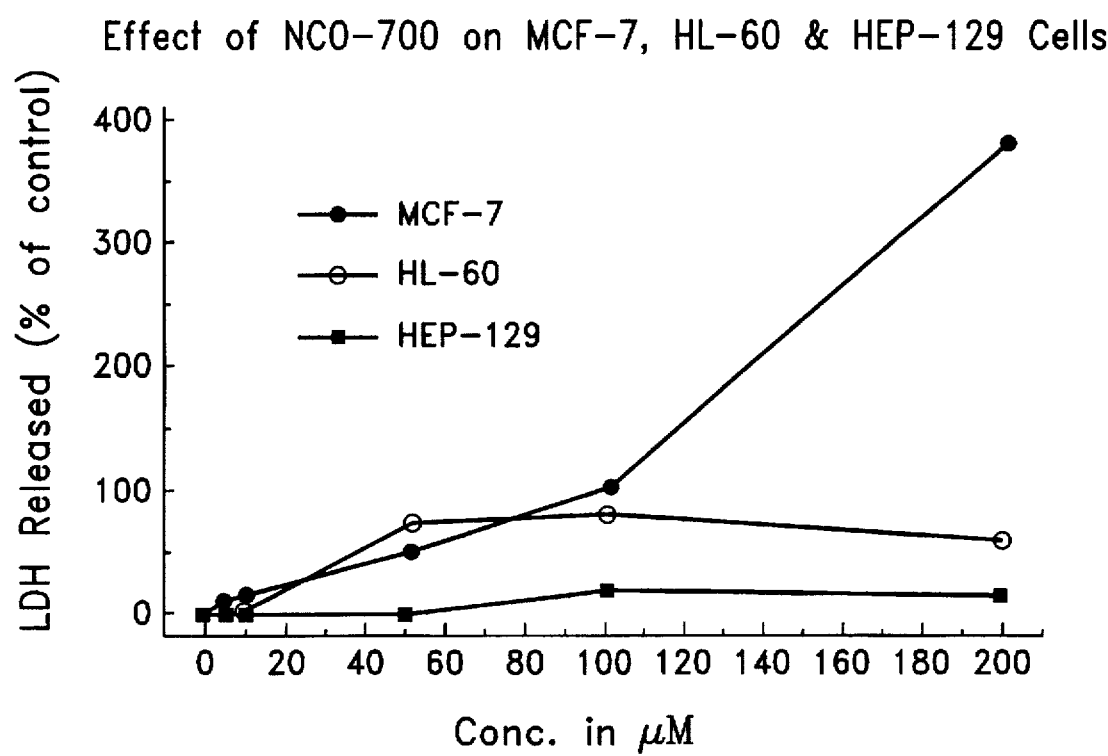
FIG. 4 is a graph showing the relationship between LDH released and the concentration of NCO-700 in cancer cell death assays of human cancer cell lines MCF-7 (breast), HL-60 (leukemia), and HEP-129 (liver).
Figure 5:
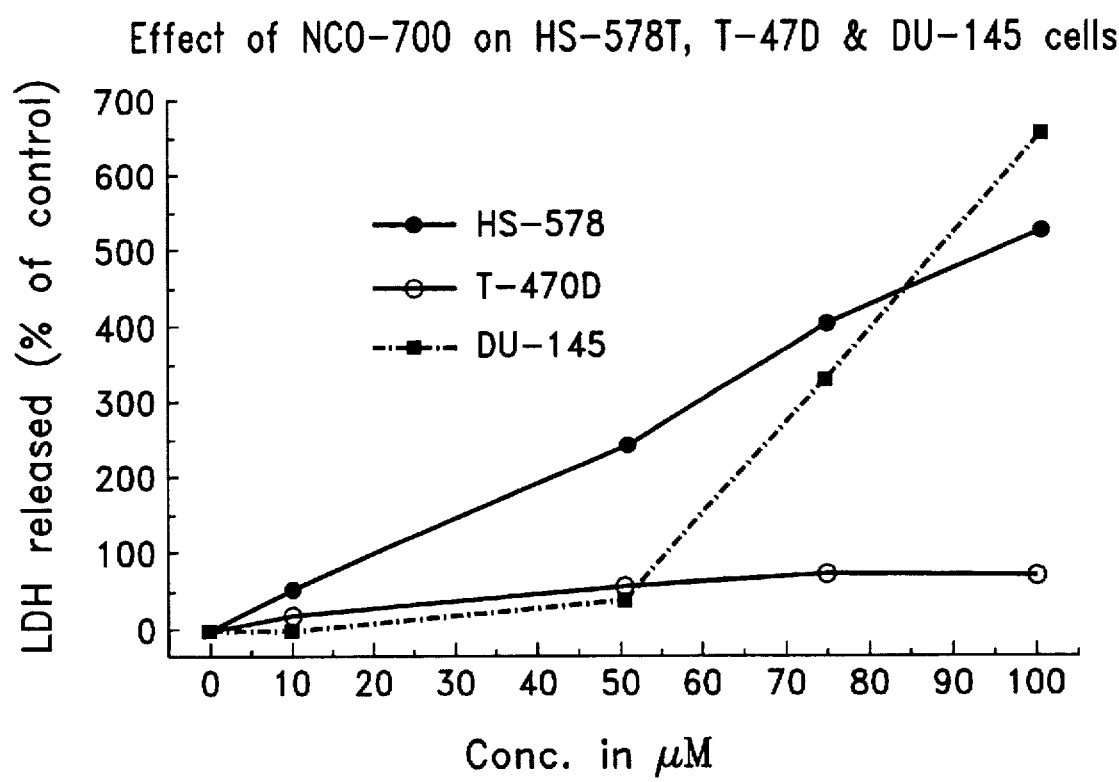
FIG. 5 is a graph showing the relationship between LDH released and the concentration of NCO-700 in cancer cell death assays of human cancer cell lines HS-578T (breast), T-47D (breast), and DU-145 (prostate).
Figure 6:
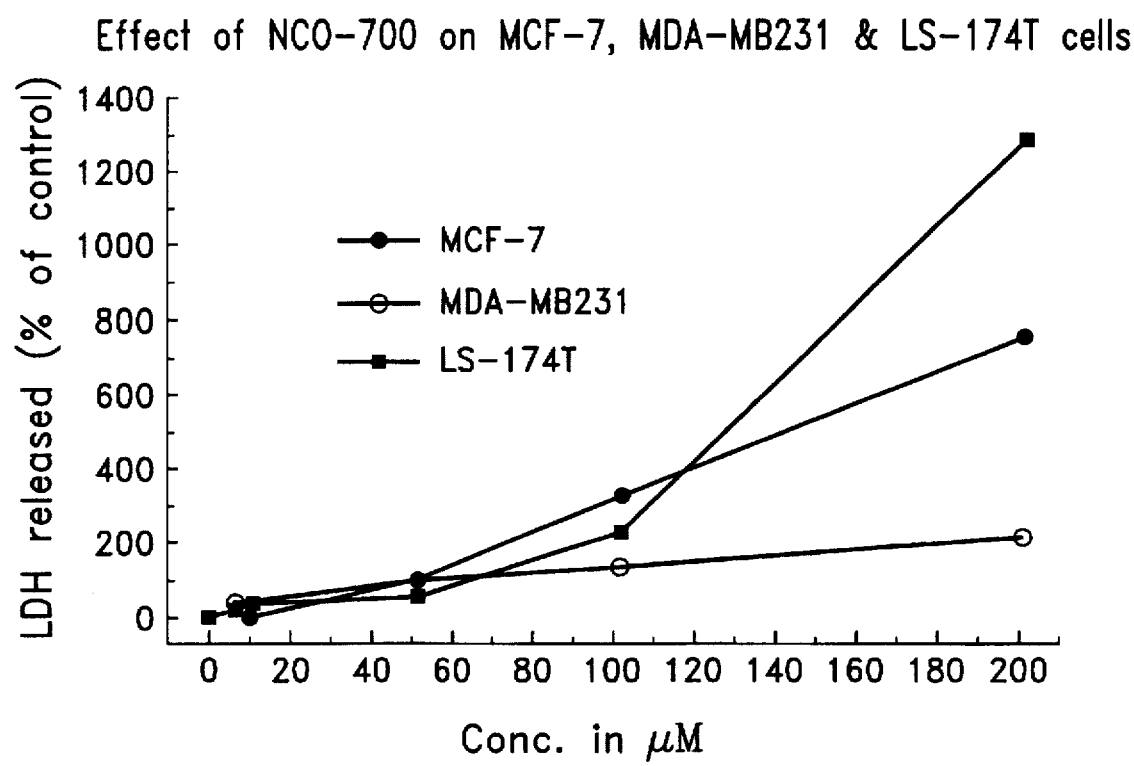
FIG. 6 is a graph showing the relationship between LDH released and the concentration of NCO-700 in cancer cell death assays of human cancer cell lines MCF-7 (breast), MDA-MB231 (breast), and LS-174T (colon).

We have discovered that piperazine derivatives having epoxy groups in the present invention can be used to kill tumor cells in vivo. Our studies show that, when the derivatives are administered to nude mice carrying a drug-resistant human tumor, there is a decline, by 60%, for example, of tumor mass without any corresponding loss of body weight. Moreover, the drugs are effective, either alone or in combination therapy, even against cancer cells exhibiting multi drug resistance.

As discussed hereinabove in the background of the invention, a major factor limiting the clinical usefulness of anticancer drugs is the development of drug resistance in tumors. Recent research indicates that two major mechanisms which underlie drug resistance in cancer cells include (i) amplification of the mdr multigene family and (ii) inhibition of programmed cell death (apoptosis). The mechanism of drug resistance in cells where the mdr gene is amplified resides in the active pumping of cancer drugs out of the cancer cell by the mdr protein which effectively lowers the concentration of anticancer drugs within the cancer cell. The second major mechanism of drug resistance in cancer cells, which only recently has been recognized, is the inhibition of programmed cell death, or apoptosis, which leads to resistance not only to chemotherapy, but radiation therapy as well (Desoize B., *Anticancer Res.* 14:221–2294, 1994). The best-characterized inhibitor of apoptosis is the protein product of the Bcl-2 gene, which is over-expressed in cancer cells that are drug and radiation resistant. A variety of rapid and distinct molecular events occur in apoptotic cells, such as nuclear chromatin condensation, changes in cell size, and activation of endogenous endonuclease activity that results in the production of oligosomal DNA fragments. Multidrug-resistant cancer cells have the apoptosis inhibition activity.

We have discovered that the piperazine derivatives having epoxy groups in the present invention are highly effective in reversing drug resistance in human cancer cells and tumors that are resistant to anticancer drugs. The derivatives can stimulate 5-fold the accumulation of the anticancer drug, vinblastine, in human carcinoma cell lines, for example. This results in a highly significant increase in the killing of these cancer cells as determined in a cancer cell survival assay. These studies indicate the piperazine derivatives having epoxy groups have significant activity in sensitizing drug-resistant cancer cells to the killing effect of anticancer drugs and demonstrates the high potential thereof for use in cancer patients.

As discussed in greater detail below, it is believed that the pharmaceutical compositions of the present invention are effective in inducing apoptosis in cancer cells. Thus, these compositions are advantageously effective in overcoming both of the major known mechanisms of drug resistance in cancer patients.

Piperazine Derivatives Having Epoxy Groups

The piperazine derivatives having epoxy groups in the present invention are compounds represented by formula I,

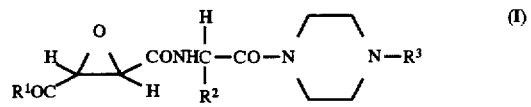

where $R^1$ is hydroxyl, C1–4 alkoxyl, C1–4 alkylcarbonyloxymethoxyl, phenyl C1–2 alkylamino group, 2,5-pyrrolidinedione-1-alkoxyl (C1–4), or

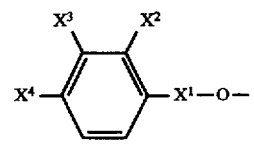

wherein $X^1$ is a chemical bond or C1–2 alkylene, $X^2$ is hydrogen or carboxyl forming a 5-membered ring with $X^1$ when $X^1$ is methylene, $X^3$ is hydrogen or C1–2 alkyl, $X^4$ is hydrogen or C1–2 alkyl, or $X^3$ and $X^4$ together form a 5-membered ring, in which at least one of $X^2$, $X^3$, and $X^4$ is hydrogen.

$R^2$ is C3–4 alkyl, $R^3$ is C1–4 alkyl,

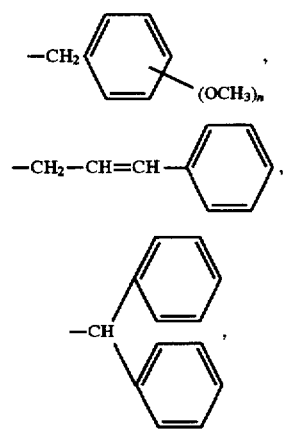

-continued

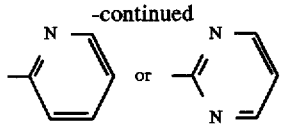

in which n is an integer of 0 to 3.

The compounds represented by formula I are typically of the following formula:

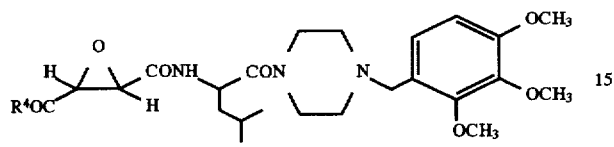

where $R^4$ is selected from the group consisting of:

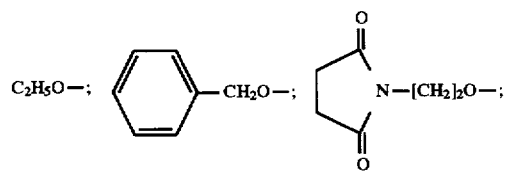

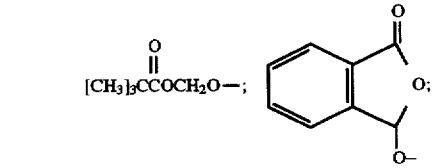

Also, other typical compounds are of the following formula:

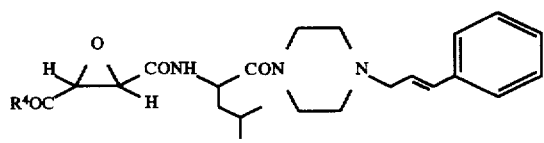

where $R^4$ is selected from the group consisting of:

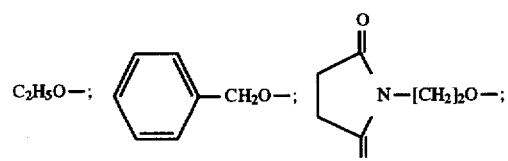

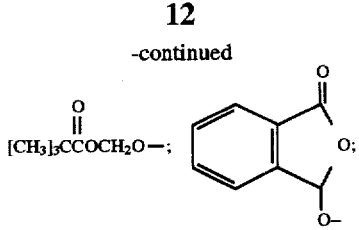

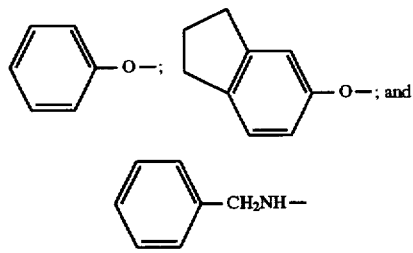

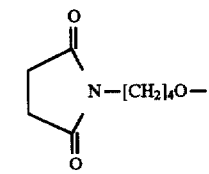

Examples of the compounds typically include the following substituents:

General Formula

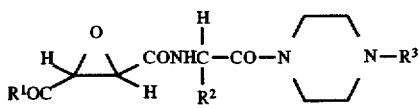

$R^1$

| | |
|---|---|
| HO— | A. |
| $CH_2H_5O—$ | B. |
| $(CH_3)_2CHCH_2O—$ | C. |
| $CH_3COCH_2O—$ (C=O) | D. |
| $[CH_3]_2CHCOCH_2O—$ (C=O) | E. |
| $[CH_3]_2C_2H_3COCH_2O—$ (C=O) | F. |
| $[CH_3]_3CCOCH_2O—$ (C=O) | G. |
| Ph-$CH_2NH—$ | H. |
| Ph-$[CH_2]_2NH—$ | I. |
| succinimide-$N—[CH_2]_4O—$ | J. |

-continued

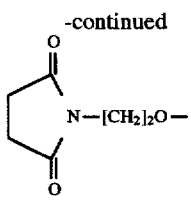

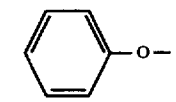

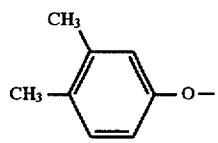

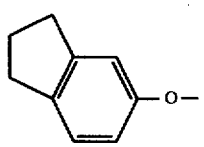

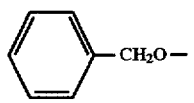

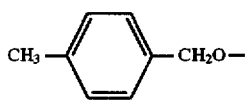

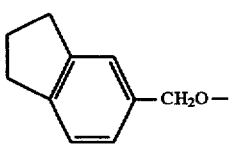

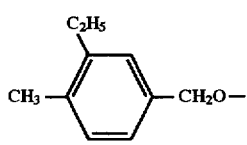

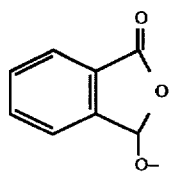

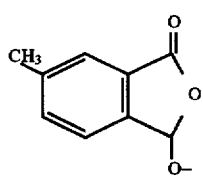

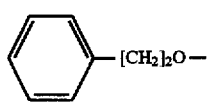

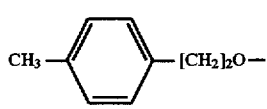

$R^2$

K. A: —$(CH_2)_2CH_3$
B: —$CH_2CH(CH_3)_2$
C: —$C(CH_3)_3$ $R^3$

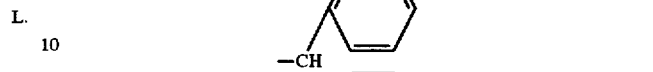   A.

L.

M.

   B.

N.

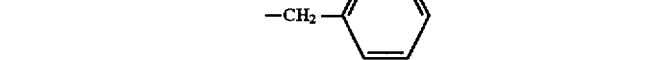   C.

O.

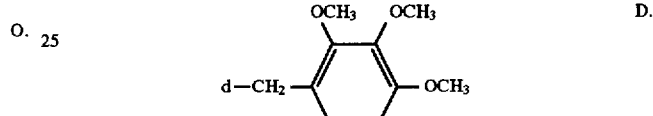   D.

P.

—$C_2H_5$   E.

F.

Q.  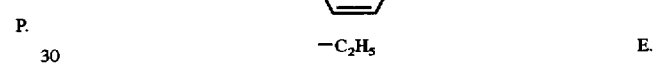

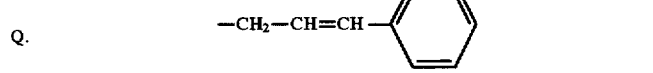   G.

R.

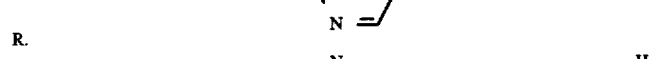   H.

S. Typical compounds included in the piperazine derivatives having epoxy groups are as follows:

| No. | $R^1$ | $R^2$ | $R^3$ | Remarks |
|-----|-------|-------|-------|---------|
| 1 | A | B | A | trans, sodium |
| 2 | A | B | B | trans, sodium |
| 3 | A | B | C | trans, sodium |
| 4 | A | B | D | trans, sodium |
| 5 | A | B | D | (2R,3R), sodium |
| 6 | A | B | D | (2S,3S), sodium |
| 7 | A | B | E | trans, sodium |
| 8 | A | B | F | trans, sodium |
| 9 | A | B | G | trans, sodium |
| 10 | A | B | H | trans, sodium |
| 11 | A | B | H | trans, sodium |
| 12 | A | B | H | trans, sodium |
| 13 | B | B | D | trans, sodium |
| 14 | B | B | D | trans, sodium |
| 15 | B | B | D | (2R,3R), ½ sulfate |
| 16 | B | B | F | (2R,3R), ½ sulfate |
| 17 | B | A | D | (2R,3R), ½ sulfate |
| 18 | B | A | F | (2R,3R), ½ sulfate |
| 19 | B | C | D | (2R,3R), ½ sulfate |
| 20 | B | C | F | (2R,3R), ½ sulfate |
| 21 | C | B | D | trans, ½ sulfate |

-continued

| No. | R¹ | R² | R³ | Remarks |
|---|---|---|---|---|
| 22 | D | B | D | (2R,3R), ½ sulfate |
| 23 | E | B | D | (2R,3R), ½ sulfate |
| 24 | F | B | D | (2R,3R), ½ sulfate |
| 25 | G | B | D | (2R,3R), ½ sulfate |
| 26 | H | B | D | (2R,3R), ½ sulfate |
| 27 | H | B | F | (2R,3R), ½ sulfate |
| 28 | I | B | F | (2R,3R), ½ sulfate |
| 29 | J | B | F | (2R,3R), ½ sulfate |
| 30 | K | B | F | (2R,3R), ½ sulfate |
| 31 | L | B | D | (2R,3R), ½ sulfate |
| 32 | L | B | F | (2R,3R), ½ sulfate |
| 33 | M | B | D | (2R,3R), ½ sulfate |
| 34 | N | B | D | (2R,3R), ½ sulfate |
| 35 | O | B | D | (2R,3R), ½ sulfate |
| 36 | O | B | F | (2R,3R), ½ sulfate |
| 37 | P | B | D | (2R,3R), ½ sulfate |
| 38 | Q | B | D | (2R,3R), ½ sulfate |
| 39 | R | B | F | (2R,3R), ½ sulfate |
| 40 | S | B | F | (2R,3R), ½ sulfate |
| 41 | T | B | F | (2R,3R), ½ sulfate |
| 42 | U | B | F | (2R,3R), ½ sulfate |
| 43 | V | B | D | (2R,3R), ½ sulfate |

The specifically defined present piperazine derivatives having epoxy groups are believed to work through an epoxide group, but E-64 also contains an epoxide group. The Shoji-Kasai et al. reference described earlier discloses that E-64-d analogous to E-64 exhibits relevant effects, i.e., slowing the growth of cancer cells, and has a partially similar structure to the exemplified compounds of the present invention. However, neither E-64 nor E-64-d contains a piperazine ring, and E-64 has been found not to be particularly effective in cancer cells having multidrug resistance, despite the fact that it has been reported that E-64-d slows the growth of cancer cells. It is believed that not only epoxy group but also a piperazine ring are essential to induction of cell death in cancer. Calpain inhibitor I has been found slightly effective within the above context, but its toxicity may be an obstacle. Other compounds having similar structures to the present piperazine derivatives, with respect to piperazine rings when present, and epoxy groups, have been tested (data omitted here), but no significant effect was observed, meaning that surprising and unexpected effects on induction of cell death in cancer, i.e., reversing mdr and in inducing death of cancer cells without significant toxicity to normal tissues, which appear to be pharmacologically beyond prevention of metastasis in cancer, are found in the specifically defined present compounds.

Production of Piperazine Derivatives

The piperazine derivatives represented in formula I in the present invention can be synthesized based on a usual acid halide method or a mixed anhydride method, the details of which are set forth in U.S. Pat. Nos. 4,507,297 and 4,596,803 to Masaki et al., both entitled "Piperazine Derivatives and A Medicine Containing the Same", and Japanese Patent Laid-open Nos. 63-275575 (1988) and 63-275576 (1988), which are hereby incorporated herein by reference.

For example, in the case where $R^1$ in formula I is an alkoxyl group, a leucine derivative represented by the general formula (2), $$R^5NHCHCO_2H \atop | \atop R^2 \qquad (2)$$

where $R^2$ is the same as in formula I, and $R^5$ is a protective group for an amino group of an amino acid such as a tert-butoxycarbonyl group, or its reactive derivative, is reacted with an amino derivative represented by the general formula (3),

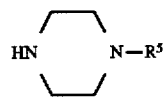

where $R^3$ is the same as defined above, to obtain a compound represented by the general formula (4),

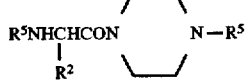

Subsequently, the protective group is removed by any conventional method, and a leucylpiperazine derivative thus obtained and represented by the general formula (5),

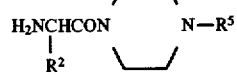

is reacted with a trans-epoxy succinic acid monoester represented by the general formula (6),

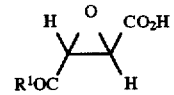

where $R^1$ is the same as in formula I, or its reactive derivative, thereby obtaining a compound represented by the general formula (7):

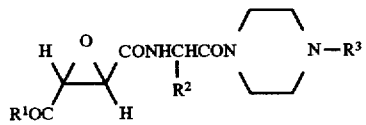

Alternatively, the trans-epoxy succinic acid monoester of the formula (6) above, or its reactive derivative, is reacted with leucine to obtain an epoxy succinyl leucine derivative represented by the general formula (8),

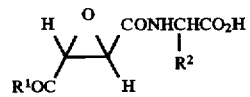

where $R^1$ is the same as in formula I except that $R^1$ is not hydroxyl group, or its reactive derivative. The compound of the formula (8) is then reacted with an amine derivative represented by the formula (3) above, thereby obtaining a compound of the formula (7) above.

In addition, the compounds of formula I can be obtained by the following condensation (dehydration) reaction:

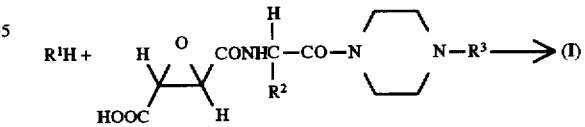

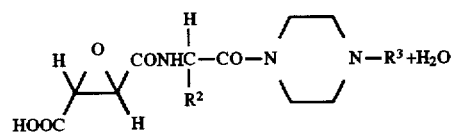

The condensation reaction of the compound of the formula (2) with the compound of the formula (3), the condensation reaction of the formula (5) with the compound of the formula (6) and the condensation reaction of the compound of the formula (8) with the compound of the formula (3) are conducted by a conventional acid halide method or a mixed anhydride method, or in an organic solvent such as methylene chloride, ethylene chloride, chloroform, ethyl acetate, tetrahydrofuran or the like in the presence of a known condensation agent such as N-hydroxy succinimide and N,N'-dicyclohexylcarbodiimide at $-10°$ to $+40°$ C., preferably at $-5°$ to $+30°$ C.

The ester residue of the compound represented by the formula (7) can be readily converted to the corresponding carboxylic acid by any existing alkaline hydrolysis method.

A compound in which $R^1$ is a hydroxyl group can be obtained by hydrolyzing the ester group of the compound of the formula (7).

The piperazine derivative thus prepared may be optionally converted to a pharmaceutically acceptable salt thereof, for example, of sodium, potassium, calcium or magnesium, or trialkylamine, dibenzlamine, N-lower alkylpiperidine, N-benzl-β-phenetylamine, α-phenethylamine, 1-(1-naphthyl)ethylamine as well as hydrochloric acid, hydrobromic acid, formic acid, sulfuric acid, fumaric acid, maleic acid or tartaric acid. Further, with use of an optically active trans-epoxy succinic acid monoester (6) such as a (2S,3S)-epoxy succinic acid monoester or a (2R,3R)-epoxysuccinic acid monoester which may be synthesized in accordance with the method of Kenji Mori et al (*Tetrahedron*, vol. 36(1), 87–90, 1980) or Japanese Patent Publication No. 3-18629 (1991), it is possible to obtain the compounds of formula I of the present invention, which has an optically active epoxy succinic acid group, by the process noted above.

Pharmaceutical Use

According to a further aspect of the invention, medicines are provided medicines for induction of cell death in cancer, which medicines contain the compounds of formula I or their pharmaceutically acceptable salts as active ingredients.

The usefulness of the compounds of formula I and their pharmaceutically acceptable salts according to the present invention as medicines for induction of cell death in cancer has been confirmed by the fact that they have superior effects in inducing apoptosis and reversal of multidrug resistance of cancer cells.

Moreover, from acute toxicity tests using mice and rats, the compounds of the invention were found to be quite safe for human use. For example, the $LD_{50}$ of NCO-700 via i.v. to rats is 317 mg/kg. This non-toxicity of the compounds makes it possible to administer the compounds to patients daily for a long period of time without interruption, without significant side effects, until the cancer tumors are suppressed. The non-toxicity, the apoptotic effects and the reversal of multidrug resistance of the compounds will change the procedures of conventional chemotherapy completely.

The dosage of the compounds of formula I and their pharmaceutically acceptable salts varies depending upon the stage of cancer development, the type of cancer, the degree of multidrug resistance thereof, and the type of chemotherapy which may be conducted concurrently. Generally, they may be administered to patients in an amount of from about 15 µg/kg to about 250 mg/kg, preferably from about 250 µg/kg to about 100 mg/kg, more preferably from about 1 mg/kg to about 50 mg/kg, to effectively cause apoptosis and reverse multidrug resistance of cancer cells. Suitable target cancers are human breast cancer cells, human melanoma cells, human ovarian cancer cells, human colon cancer cells, human pancreatic cancer cells, human prostate cancer cells, especially when these cancer cells are in the undifferentiated stage.

For various formulations as medicines, the compounds of formula I and their salts may usually be combined with pharmaceutical carriers to prepare pharmaceutical compositions. Examples of the carriers include diluents or vehicles such as a filler, a binding agent, a disintegrator and a lubricant.

Such medicines are available in the dosage form of an injection, a powder, a capsule, a granule, a tablet or an ampule.

In the case of a tablet, a carrier is used which may be selected, for example, from a vehicle such as lactose, saccharose, sodium chloride, a glucose solution, starch, calcium carbonate, crystal cellulose or silicic acid; a binder such as water, ethanol, propanol, glucose, a starch solution, a gelatin solution, caraboxylmethyl cellulose, methyl cellulose or potassium phosphate; a disintegrator such as dried starch, sodium alginate, an agar powder, sodium hydrogencarbonate, calcium carbonate, stearic acid monoglyceride, starch or lactose; or a lubricant such as a stearate, a boric acid powder or solid polyethylene glycol which is known in the art. Where it becomes desirable, the tablet may be sugar- or gelatin-coated, or film-coated.

In the case of an injection, a diluent is used which may be selected, for example, from water, ethyl alcohol, propylene glycol, polyoxyethylene sorbit or a sorbitan ester. In such instance, sodium chloride, glucose or glycerine may be added in an amount sufficient to form an isotonic solution. A commonly used dissolving aid, a buffer, a pain reliever or a preserving agent may also be conveniently incorporated.

The present piperazine derivatives can be administered singly or in combination with a chemotherapeutic agent, or with other chemotherapy such as radiation treatment. In the case of a combination of the piperazine derivatives and a chemotherapeutic agent such as vinblastine and adriamycin, the piperazine derivatives can be administered substantially contemporaneously with such a chemotherapeutic agent, so that the piperazine derivatives can be formed into any pharmaceutical forms uniformly with the chemotherapeutic agent.

This invention will be described in more detail with reference to certain specific examples and test examples which are provided for purposes of illustration only and are not construed as limiting. Each tested compound was synthesized based on the production process explained earlier. The test examples are intended to show the compounds of formula I and their pharmaceutically acceptable salts as exhibiting superior effects on apoptosis and reversal of multidrug resistance of cancer cells.

EXPERIMENT 1

Anti-neoplastic Activity of NCO-700 and Related Analogs Alone

NCO-700  Bis[ethyl (2R,3R)-3-[(S)-3-methyl-1-[4-(2,3,4-trimethoxyphenylmethyl)piperazin-1-ylcarbonyl]butylcarbamoyl]oxirane-2-carboxylate] sulfate

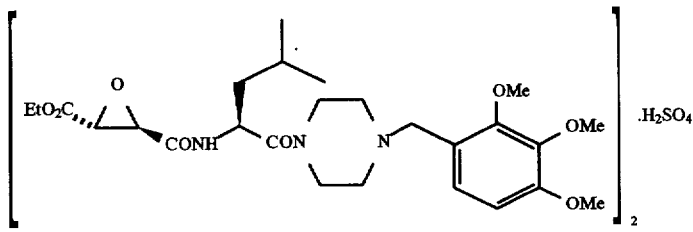

TOP-008  Bis[ethyl (2R,3R)-3-[(S)-3-methyl-1-[4-(3-phenyl-2-propenyl)piperazin-1-ylcarbonyl]butylcarbamoyl]oxirane-2-carboxylate] sulfate

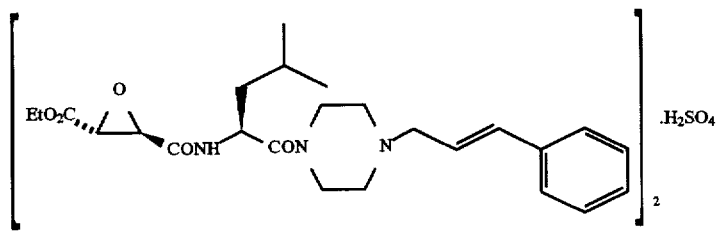

TOP-009  Bis[benzyl (2R,3R)-3-[(S)-3-methyl-1-[4-(3-phenyl-2-propenyl)piperazin-1-ylcarbonyl]butylcarbamoyl]oxirane-2-carboxylate] sulfate

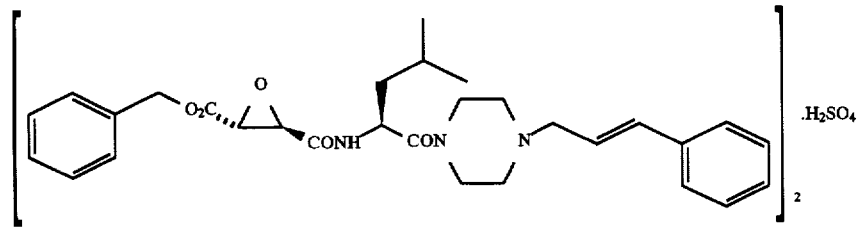

TOP-013  Bis[phenyl (2R,3R)-3-[(S)-3-methyl-1-[4-(3-phenyl-2-propenyl)piperazin-1-ylcarbonyl]butylcarbamoyl]oxirane-2-carboxylate] sulfate

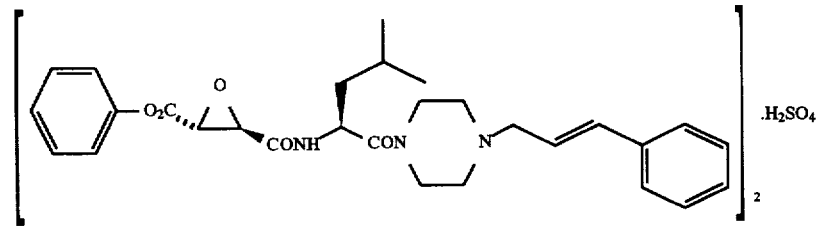

TOP-017  Bis[(2R,3R)-2-benzylcarbamoyl-3-[(S)-3-methyl-1-[4-(3-phenyl-2-propenyl)piperazin-1-ylcarbonyl]butylcarbamoyl]oxirane] sulfate

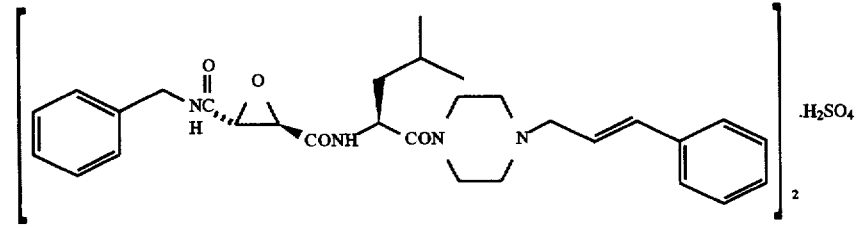

Methods

In this experiment, three different assays were utilized to measure anti-neoplastic activity of compounds.

1. Cancer Cell Death Assay: Cell death was measured quantitatively by the release of a marker intracellular enzyme, lactate dehydrogenase (LDH), from damaged or killed cells. LDH released into the extracellular fluid, was measured 24 hours after drug exposure to cancer cells and the enzyme activity was determined by the method of Decker et al. (*J. Immunolog Methods* 15:61–99, 1988).

2. Cell Survival Assays: Cell survival was assayed in cultured tumor cells. From 500–1000 cells per well were plated in 24-welled culture dishes and exposed to drug for seven days. After drug exposure, a computerized cell imaging technique was utilized to ascertain the number of viable cells remaining in each culture. From the data, survival curves were plotted and a $ED_{50}$ (drug concentration that permits 50% cell survival) were calculated.

3. In Vivo Model/Subrenal Capsule (SRC) Tumor Implant Assay: A tumor implant model, where human tumors were implanted into the renal capsule of mice was performed. The tumors successfully escaped the immune system of the mouse and grew over a six-day period. The advantage of this assay is that the effect of chemotherapeutic agents can be tested in vivo. This model was developed at the University of California, Irvine by Stratton et al. (*Gynecologic Oncology* 17:185–188, 1984). Human tumors were implanted on day one and were exposed to drug on days two-six. The size of the implant was determined at time zero and at the end of five days of drug treatment, and the difference in size of the implanted tumor at day six, when compared to control animals not exposed to drug, is referred to herein as the delta mean.

Cell Lines Utilized

All cell lines used in the present study were obtained from the American Type Tissue Culture Laboratory and cultured according to their specifications. All were human cancer lines unless otherwise noted. The following cell lines and their tissue of origin used in our studies were:

|  | Cell Line | Tissue | Comment |
|---|---|---|---|
| 1. | MCF-7 | breast | + estrogen rec |
| 2. | MDA-MB231 | breast | + estrogen rec |
| 3. | T-47D | breast | + estrogen rec |
| 4. | HS-578T | breast | − estrogen rec |
| 5. | B16F10 | melanoma | mouse line |
| 6. | SK-Mel-2 | melanoma |  |
| 7. | SW-626 | ovarian |  |
| 8. | AN-3-CA | ovarian |  |
| 9. | HL-60 | leukemia |  |
| 10. | Hep-129 | liver |  |
| 11. | LS-174T | colon |  |
| 12. | WIDR | colon |  |
| 13. | DU-145 | prostate | − testosterone rec |
| 14. | PC-3 | prostate | − testosterone rec |
| 15. | LN | prostate | + testosterone rec |

Results

1) NCO-700 and Cancer Cell Death: The first assays performed measured the anti-neoplastic activity of NCO-700, alone, in cell death assays of a wide variety of human cancer cells. The results of these experiments are shown in FIGS. 1–6, where a dose-response curve of NCO-700 versus % LDH release is plotted, with higher values of LDH released indicating greater anti-neoplastic activity (apoptosis). From these assays, it can be seen that (i) in breast cancer cells lines, the cells that were responding to NCO-700 were estrogen receptor negative, a trait generally associated with a more undifferentiated, and hence, more malignant tumor; (ii) in the melanoma group, all cells lines showed sensitivity to NCO-700; (iii) in the prostate cancer cell lines, the cell lines that were testosterone receptor negative (and more malignant) responded very well to NCO-700; (iv) the colon and ovarian cancer cell lines were partly responsive; and (v) the leukemia and liver cancer cell lines did not respond to NCO-700. However, as shown in the experiment described later (Experiment 7), NCO-700 has significant anti-neoplastic activities when used in conjunction with a standard chemotherapeutic agent such as vinblastine and adriamycin on drug-resistant tumors, even when NCO-700 is not significantly effective in apoptosis of the tumors.

Figure 7:
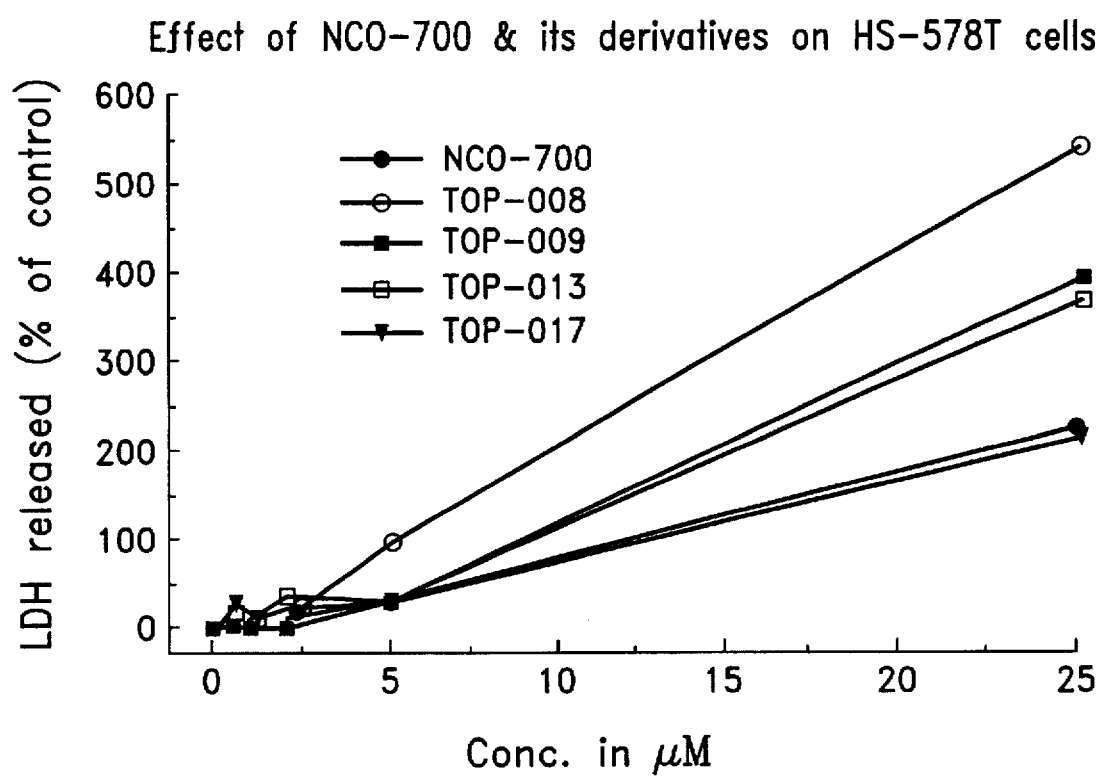
FIG. 7 is a graph showing the relationship between LDH released and the concentration of NCO-700, TOP-008, TOP-009, TOP-013, and TOP-017 in cancer cell death assays of human cancer cell line HS-578T (breast).

2) NCO-700 Analogs and Cell Death: A series of analogs related to NCO-700 were assayed in the cancer cell death assay. As shown in FIG. 7, a number of these analogs had significant anti-neoplastic activity as measured by LDH release from HS-578T, a breast cancer cell line. When compared to NCO-700, three analogs showed higher potency including analogs TOP-008, TOP-009 and TOP-013. In particular, TOP-008 showed the highest potency with an approximately three-fold higher kill rate of breast cancer cells than NCO-700. It should be stressed that these analogs were tested alone, without any added chemotherapeutic agent.

Figure 8:
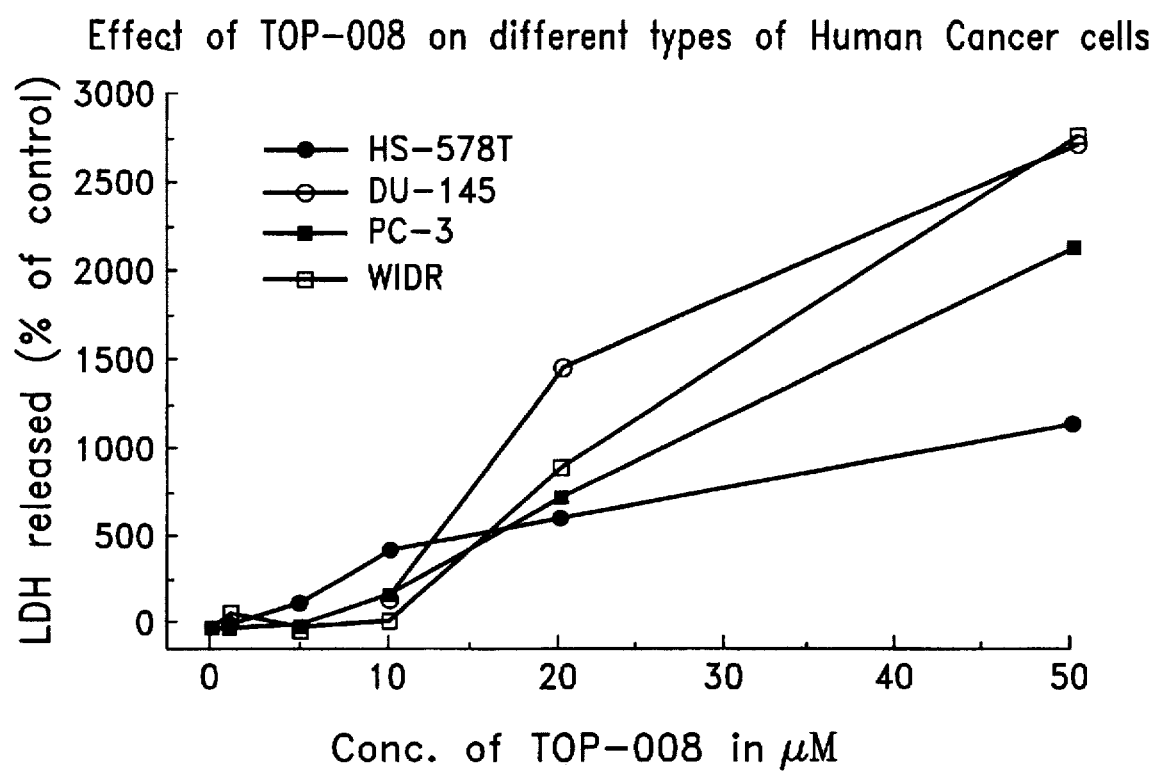
FIG. 8 is a graph showing the relationship between LDH released and the concentration of TOP-008 in cancer cell death assays of human cancer cell lines HS-578T (breast), DU-145 (prostate), PC-3 (prostate), and WIDR (colon).
Figure 9:
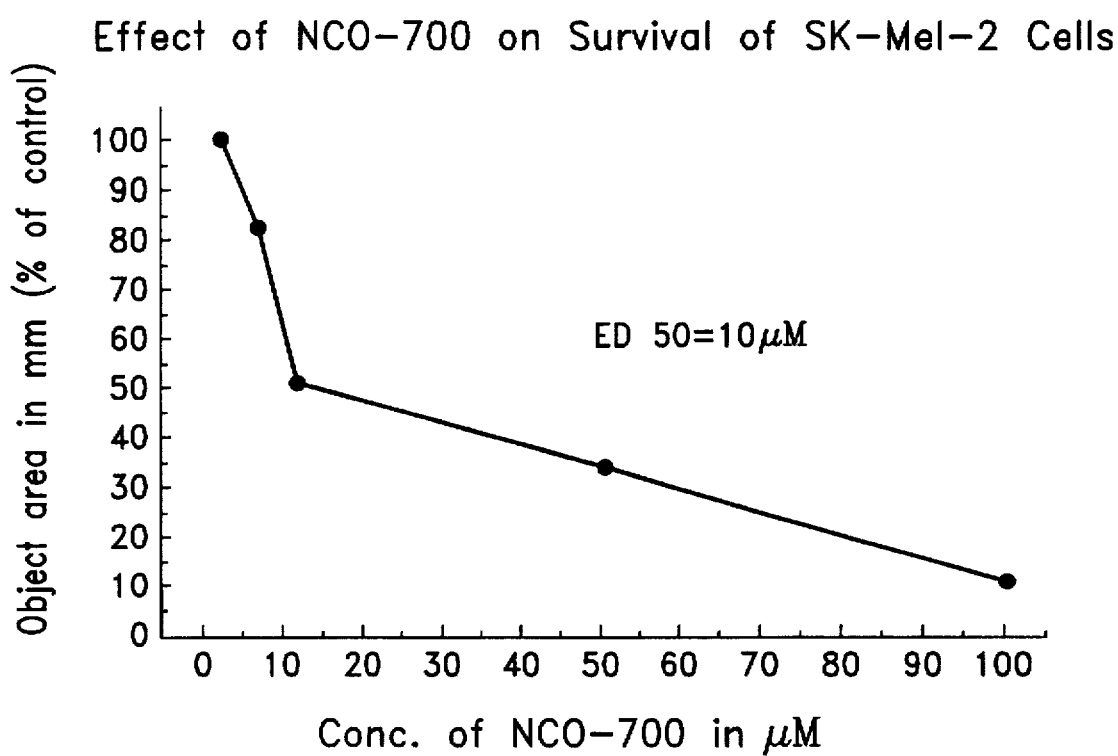
FIG. 9 is a graph showing the relationship between the object area (the number of surviving cancer cells calculated by a computer) and the concentration of NCO-700 in a cancer cell survival assay of human cancer cell line SK-Mel-2 (melanoma).
Figure 10:
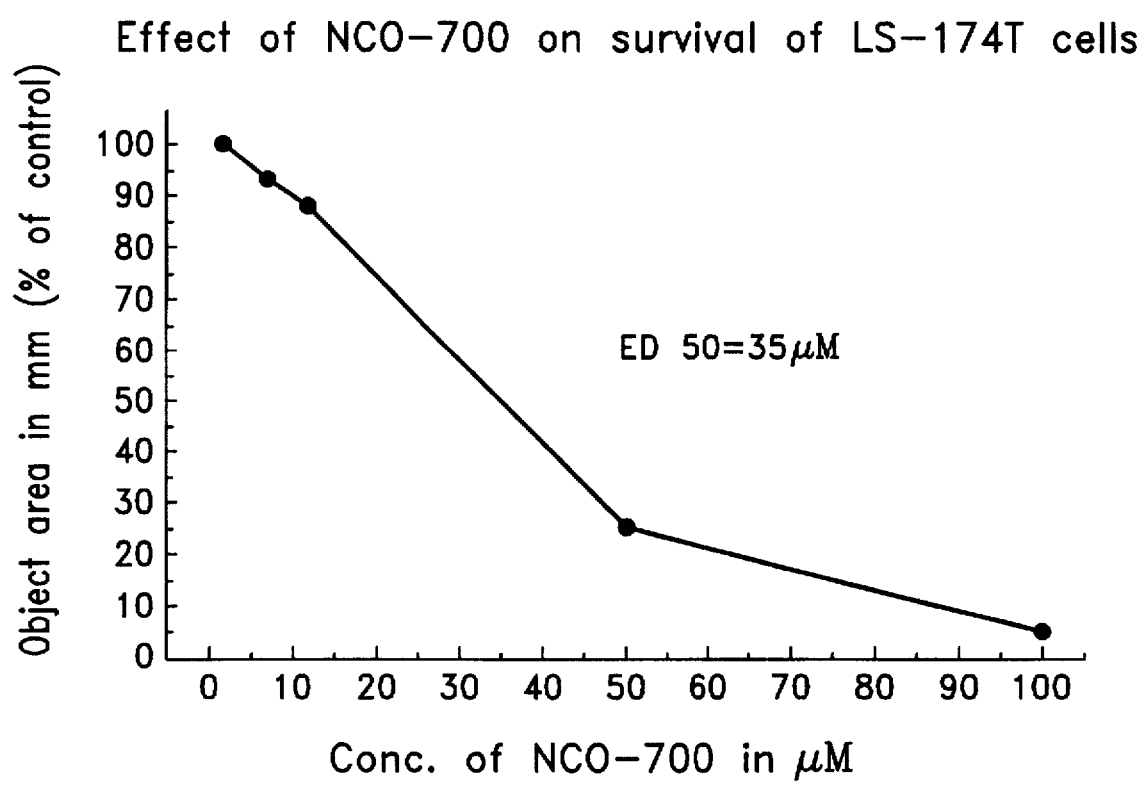
FIG. 10 is a graph showing the relationship between the object area and the concentration of NCO-700 in a cancer cell survival assay of human cancer cell line LS-174T (colon).
Figure 11:
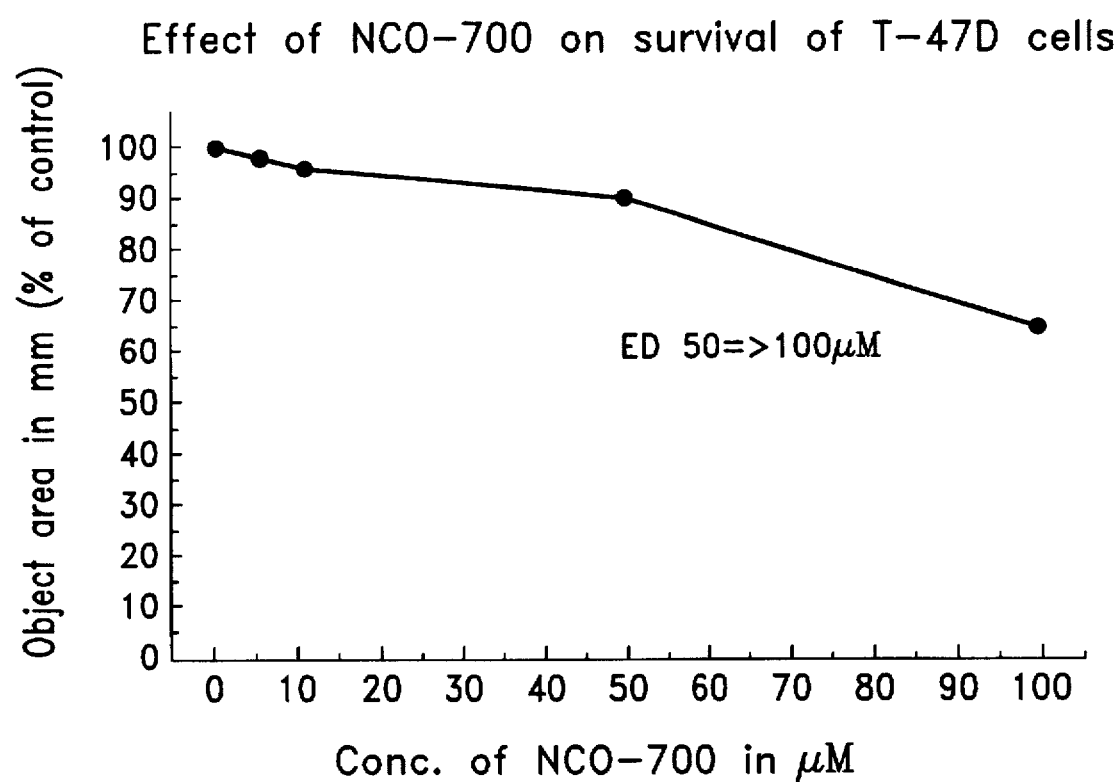
FIG. 11 is a graph showing the relationship between the object area and the concentration of NCO-700 in a cancer cell survival assay of human cancer cell line T-47D (breast).
Figure 12:
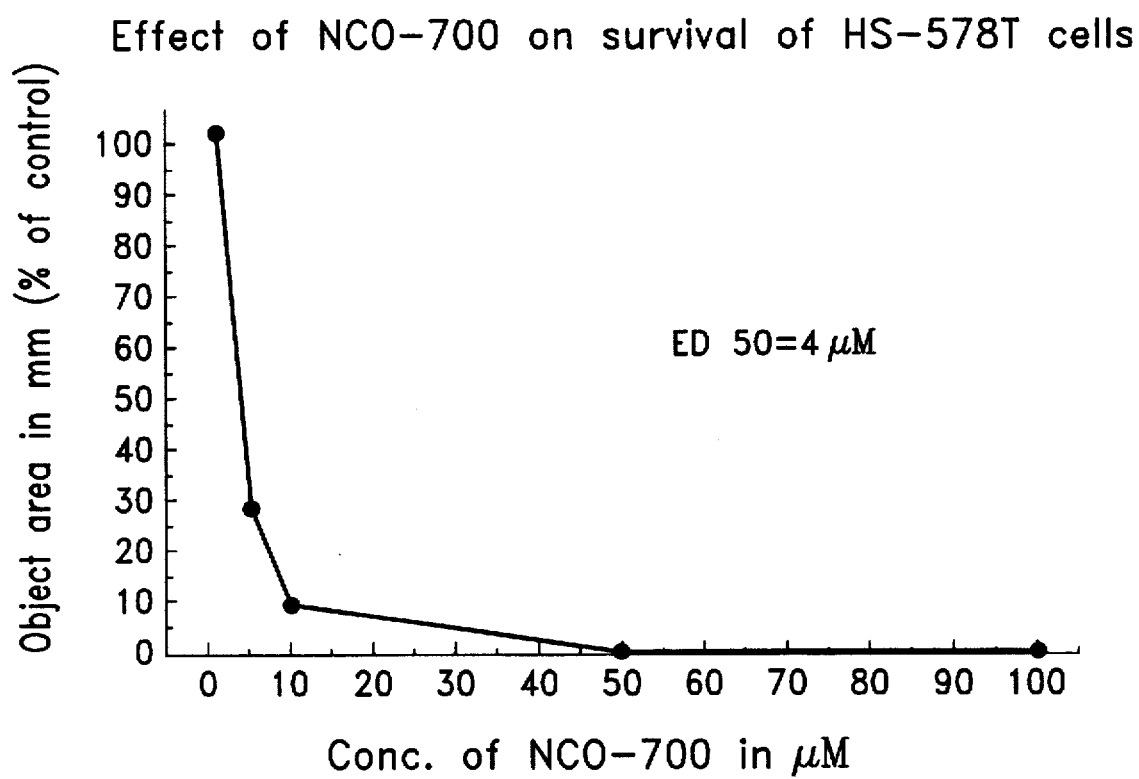
FIG. 12 is a graph showing the relationship between the object area and the concentration of NCO-700 in a cancer cell survival assay of human cancer cell line HS-578T (breast).
Figure 13:
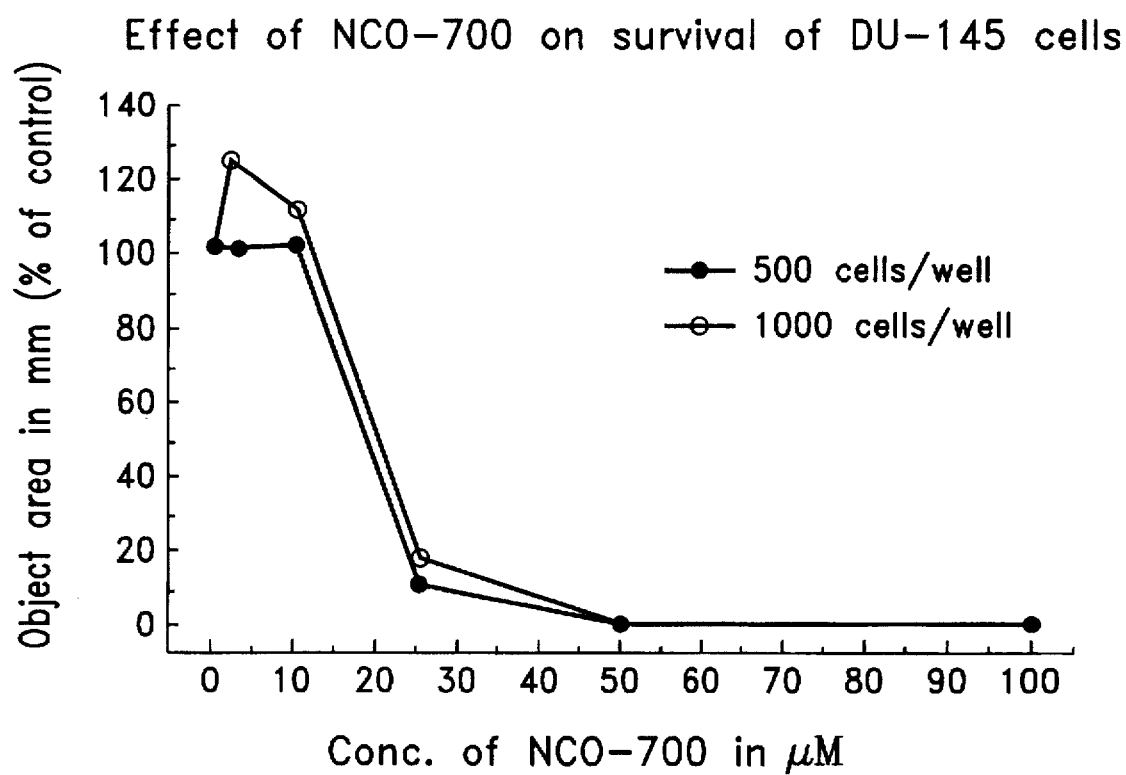
FIG. 13 is a graph showing the relationship between the object area and the concentration of NCO-700 in cancer cell survival assays of human cancer cell line DU-145 (prostate) of 500 cells/well and 1,000 cells/well.
Figure 14:
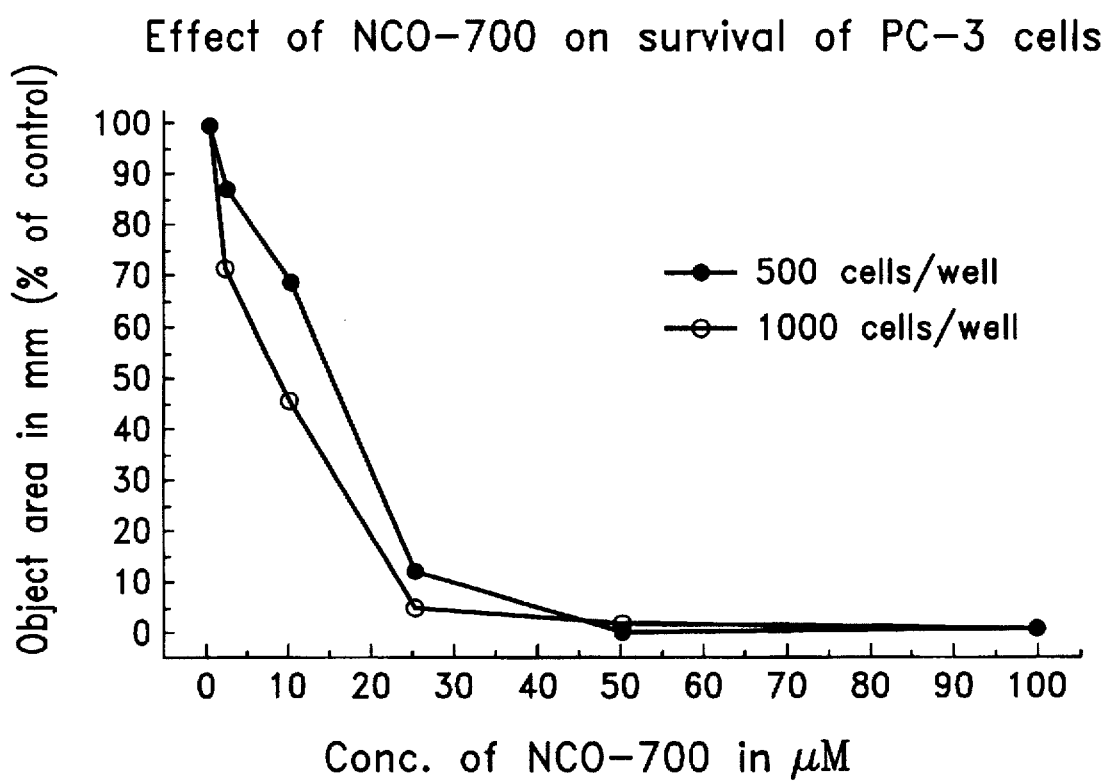
FIG. 14 is a graph showing the relationship between the object area and the concentration of NCO-700 in cancer cell survival assays of human cancer cell line PC-3 (prostate) of 500 cells/well and 1,000 cells/well.
Figure 15:
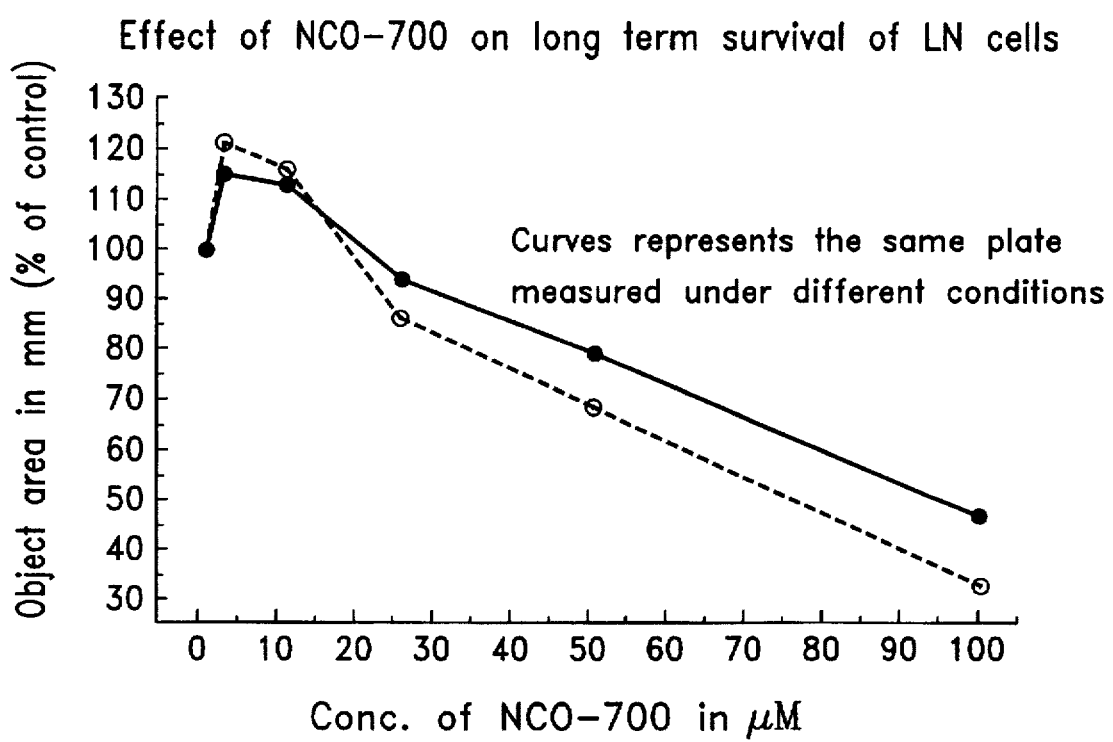
FIG. 15 is a graph showing the relationship between the object area and the concentration of NCO-700 in cancer cell survival assays of human cancer cell line LN (prostate).
Figure 16:
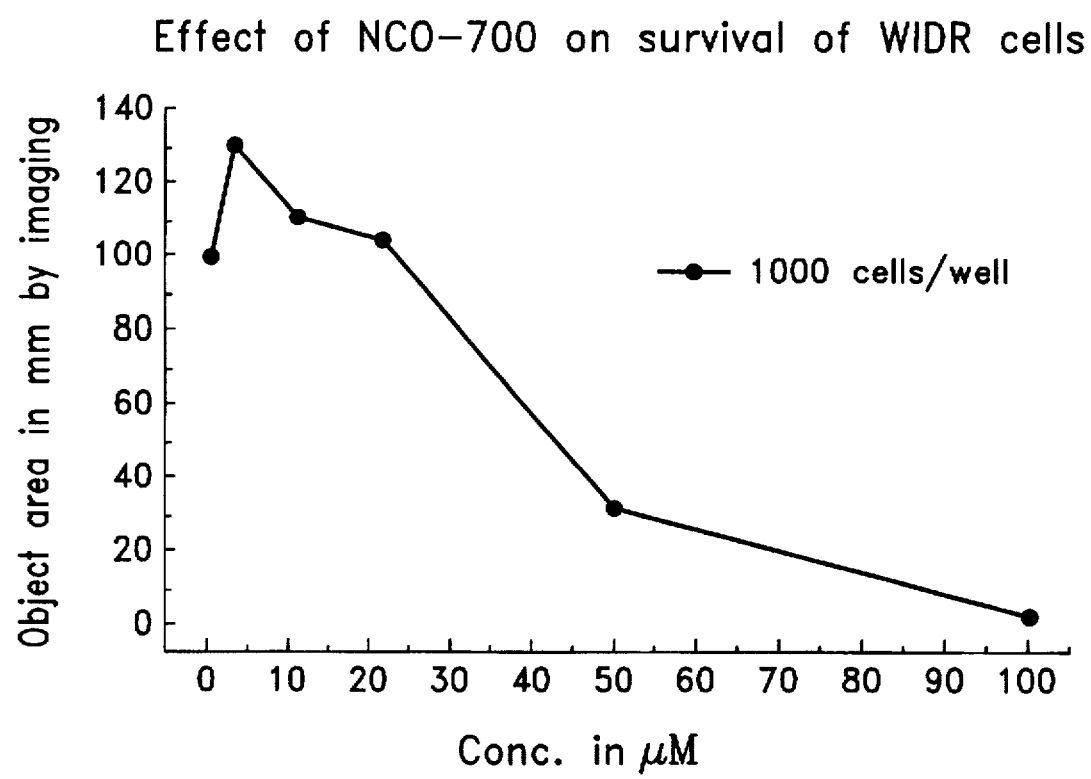
FIG. 16 is a graph showing the relationship between the object area and the concentration of NCO-700 in cancer cell survival assays of human cancer cell line WIDR (colon) of 1,000 cells/well.

As TOP-008 appeared to be the most potent NCO-700 analog tested to date in vitro, its anti-neoplastic activity was examined against other cancer cell lines. In FIG. 8, a dose-response curve is shown of the effect of TOP-008 on the killing of breast, prostate and colon cell lines. This analog, on its own, shows excellent activity against these cancer cell lines.

3) NCO-700 and Cancer Cell Survival Assay: The cancer cell survival assay is an important additional in vitro assay to assess the anti-neoplastic activity of compounds as the cells are given a prolonged exposure (seven days) to the drug. FIGS. 9–16 show the effect of increasing the dose of NCO-700 on the survival of a number of cancer cell lines. The survival studies confirm the results that were obtained with the cell death assay, namely that NCO-700 has significant anti-neoplastic activity, alone, against a number of human cancers (breast cancer cell lines T-47D and HS-578T, colon cancer cell lines LS-174T and WIDR, and prostate cancer cell lines DU-145, PC-3, and LN). In the figures, the vertical axis is the object area, which is the number of surviving cancer cells calculated by a computer.

Figure 17:
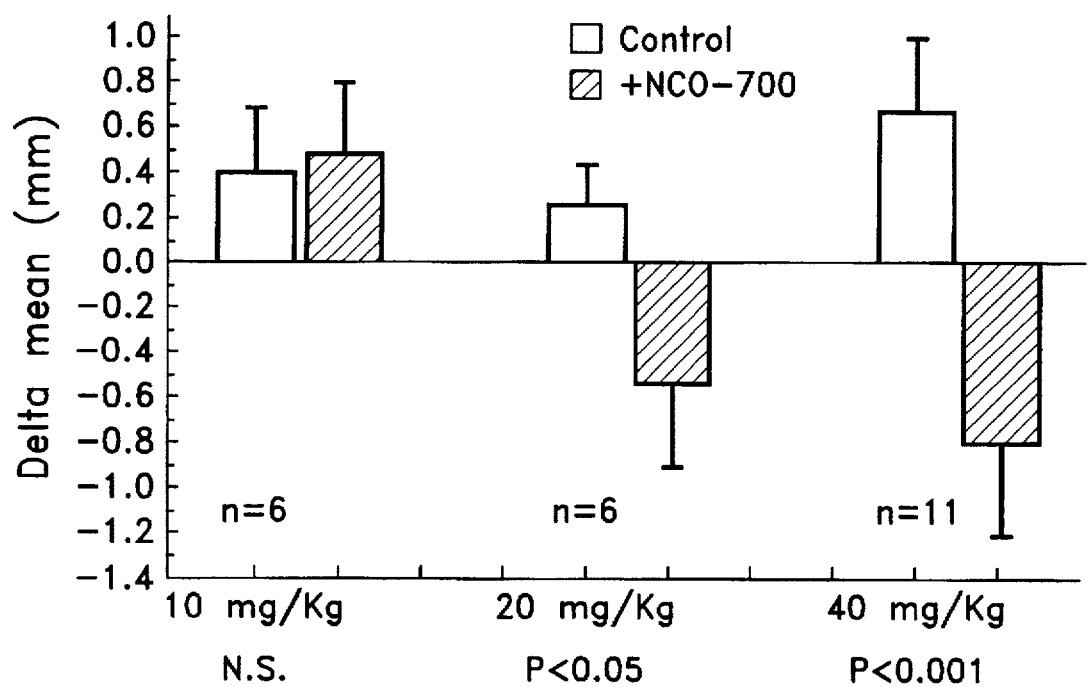
FIG. 17 is a graph showing the relationship between the mean change in size of tumor (delta mean) and the dosage of NCO-700 in a sub-renal capsule assay of human prostate cancer in BDF/1 mice.

4) NCO-700 Effect on Human Prostate Cancer Cells Grown In Vivo in the SRC Assay: Human cancer cells can be grown in the sub-renal capsule of mice, where for a limited period of time they escaped the detection of the mouse's immune system. This assay provides a convenient system to study the effect of drugs on the growth of tumor cells in vivo. As this is a much more time-consuming assay, and requires more drug than the in vitro assays, the effect of NCO-700 was tested on a single prostate cancer cell line. Three groups of animals (n=23 total) were tested with three concentrations of NCO-700 including, 10 mg/kg, 20 mg/kg and 40 mg/kg. As shown in FIG. 17, there is a does response effect of NCO-700 in decreasing the size of the tumor in the mice. Whereas the 10 mg/kg had no effect, there was a significant anti-neoplastic effect of NCO-700 at the 20 mg/kg and 40 mg/kg level. At 40 mg/kg the effect of NCO-700 was highly significant with a P value >0.001 (see FIG. 17). Again, the anti-tumor effect was seen with NCO-700 alone without any additional drugs added and points to the high potential of this and related compounds as new anti-neoplastic agents.

Figure 18:
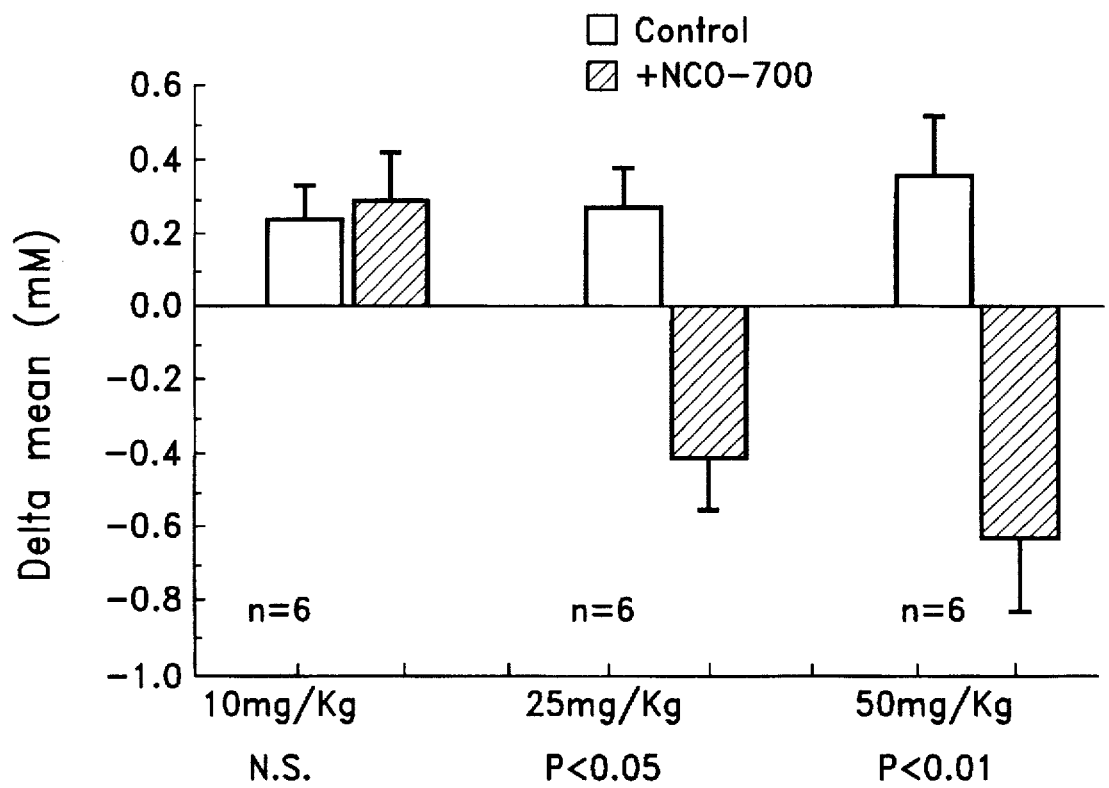
FIG. 18 is a graph showing the relationship between the change in size of tumor and the dosage of NCO-700 in a sub-renal capsule assay of human breast cancer in BDF/1 mice.

5) NCO-700 Effect on Human Breast Cancer Cells Grown In Vivo in the SRC Assay: The effect of NCO-700 on a breast cancer line was tested in the SRC assay. Three groups of animals (n=18 total) were tested with three concentrations of NCO-700 including, 10 mg/kg, 25 mg/kg and 50 mg/kg. As shown in FIG. 18, there is a dose response effect of NCO-700 in decreasing the size of the tumor in the mice. Whereas the 10 mg/kg had no effect, there was a significant anti-neoplastic effect of NCO-700 at the 25 mg/kg and 50 mg/kg level. These studies confirm the high potential of NCO-700 and related compounds as new anti-neoplastic agents.

Figure 19:
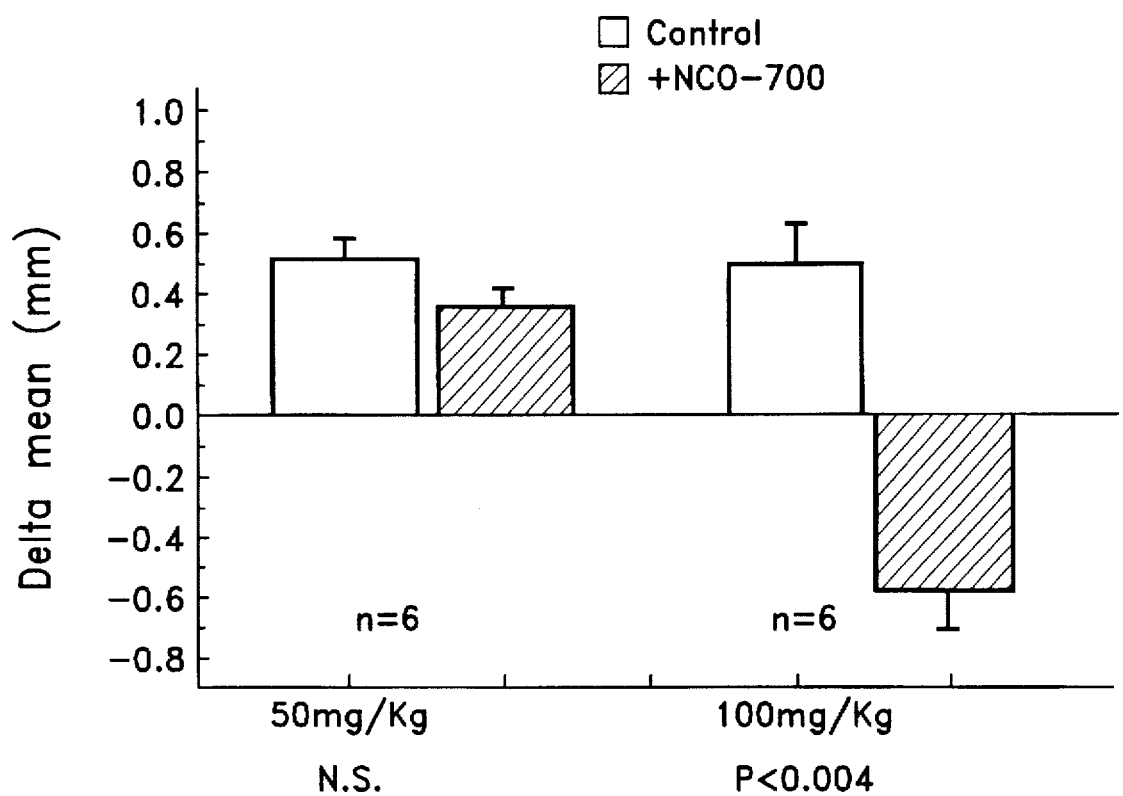
FIG. 19 is a graph showing the relationship between the change in size of tumor and the dosage of NCO-700 in a sub-renal capsule assay of human colon cancer in BDF/1 mice.
Figure 20:
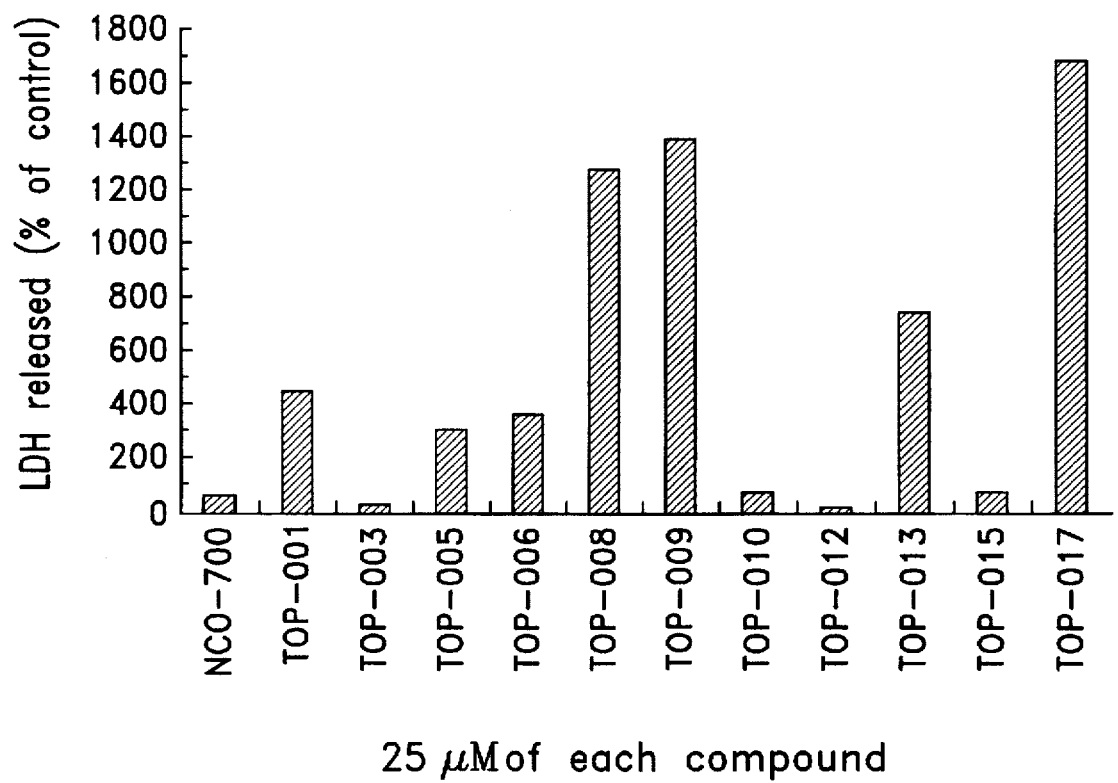
FIG. 20 is a graph showing the LDH release stimulated by NCO-700, TOP-008, and analogs in cancer cell death assays of human cancer cell line DU-145 (prostate) at a concentration of 25 µM.
Figure 21:
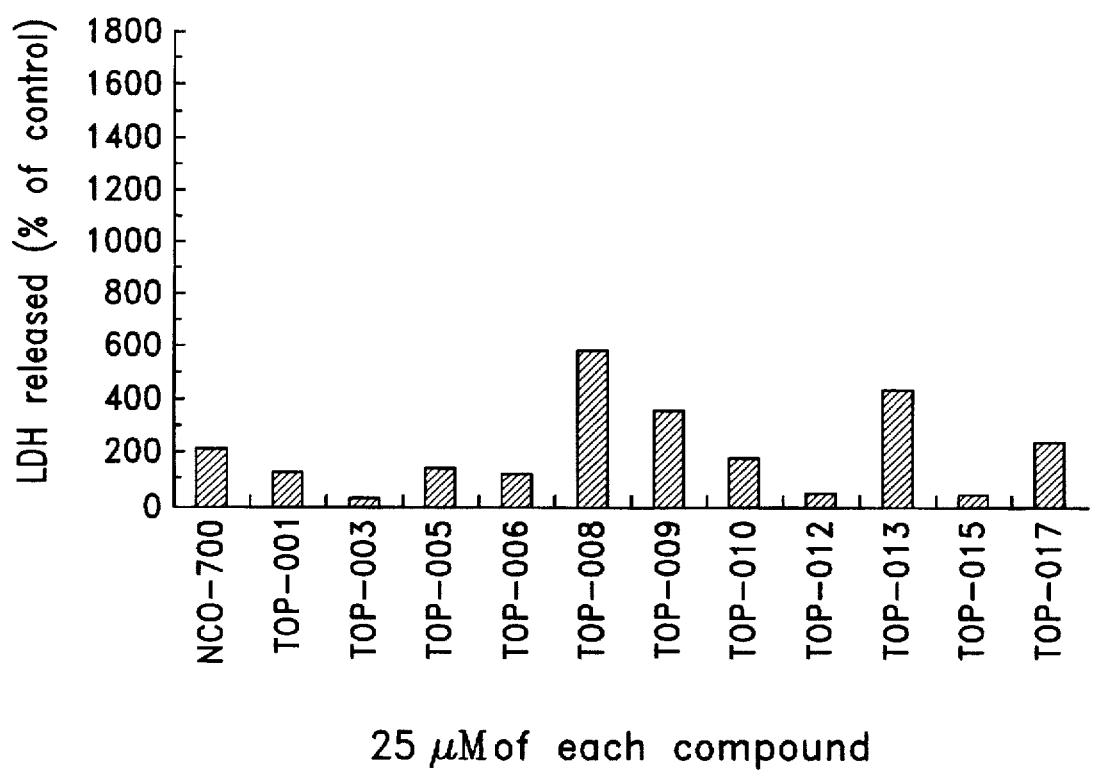
FIG. 21 is a graph showing the LDH release stimulated by NCO-700, TOP-008, and analogs in cancer cell death assays of human cancer cell line HS-578T (breast) at a concentration of 25 µM.
Figure 22:
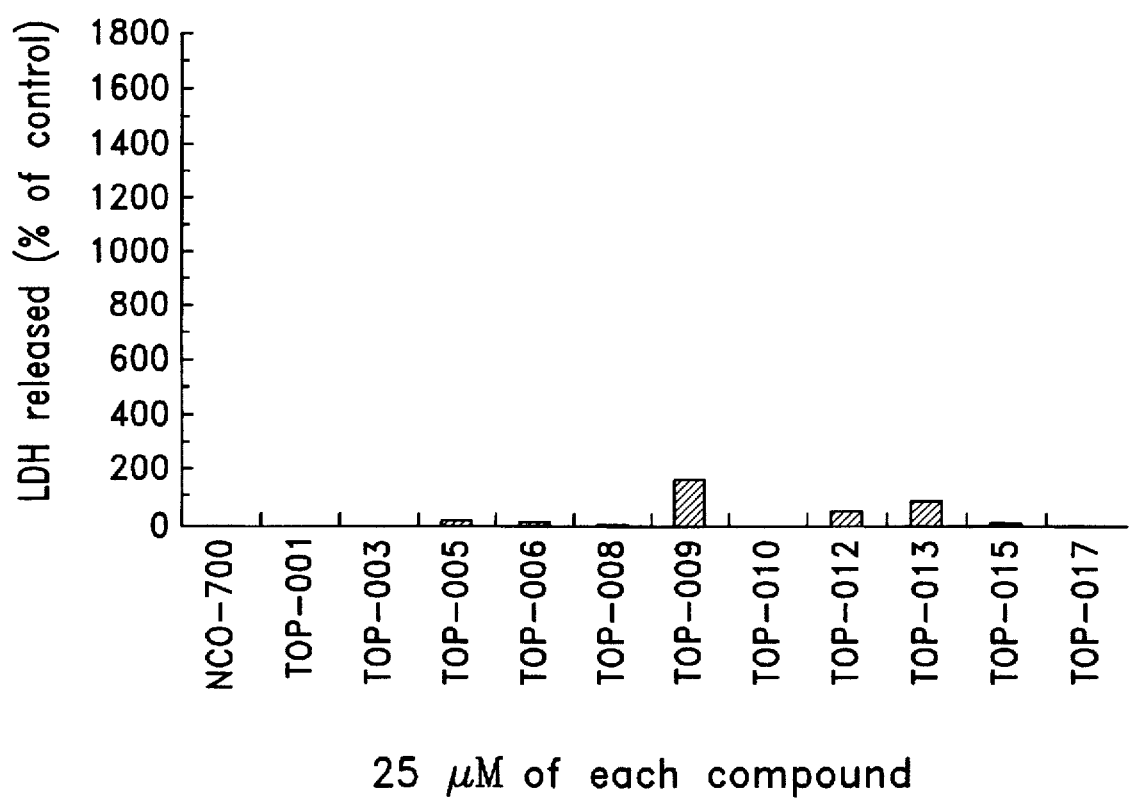
FIG. 22 is a graph showing the LDH release stimulated by NCO-700, TOP-008, and analogs in cancer cell death assays of human cancer cell line T-47D (breast) at a concentration of 25 µM.
Figure 23:
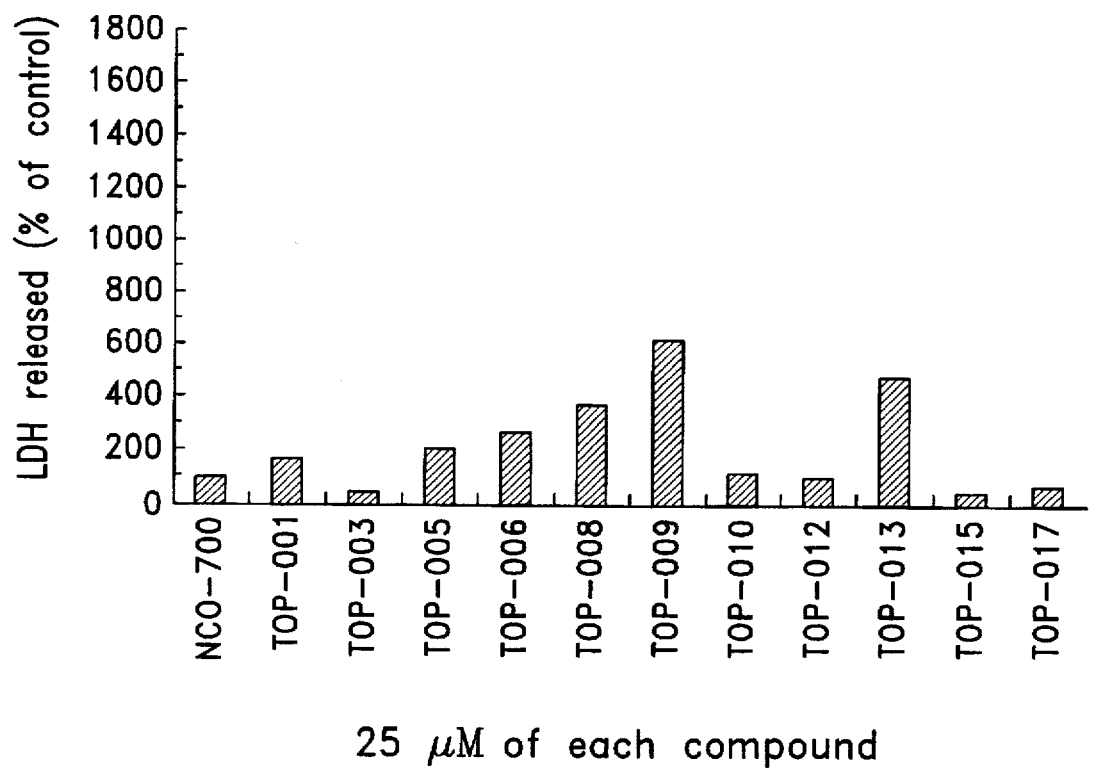
FIG. 23 is a graph showing the LDH release stimulated by NCO-700, TOP-008, and analogs in cancer cell death assays of human cancer cell line SK-MEL-2 (melanoma) at a concentration of 25 µM.
Figure 24:
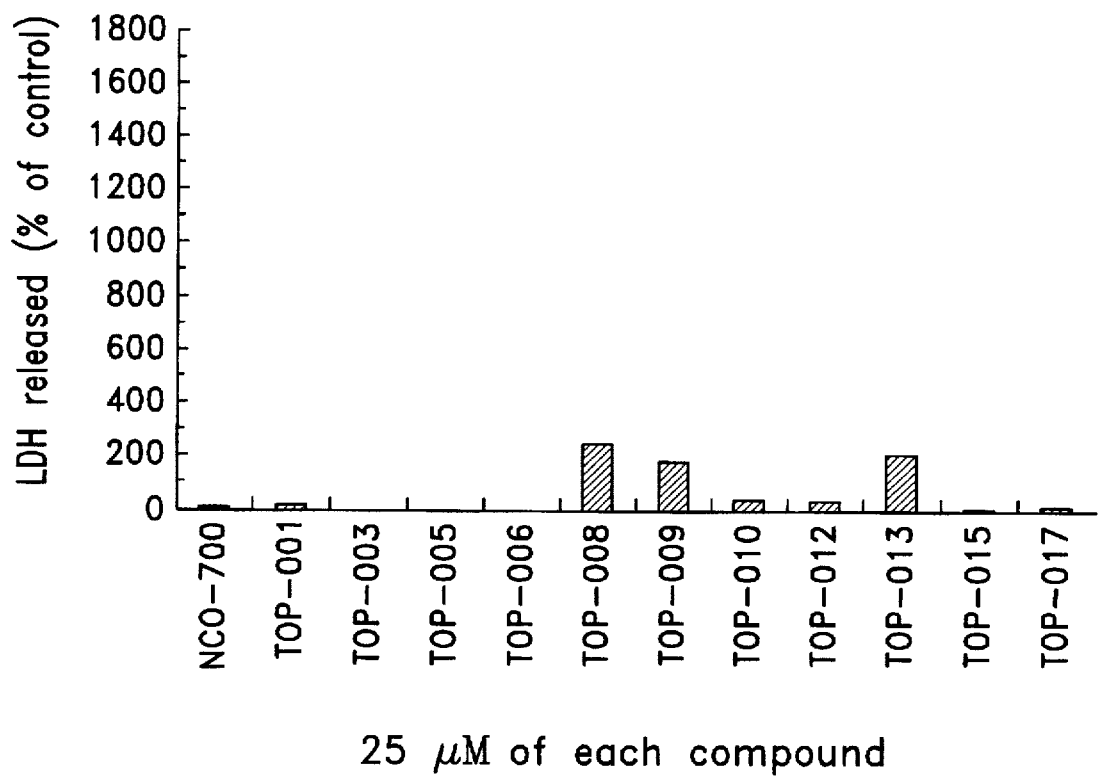
FIG. 24 is a graph showing the LDH release stimulated by NCO-700, TOP-008, and analogs in cancer cell death assays of human cancer cell line WIDR at a concentration of 25 µM.
Figure 25:
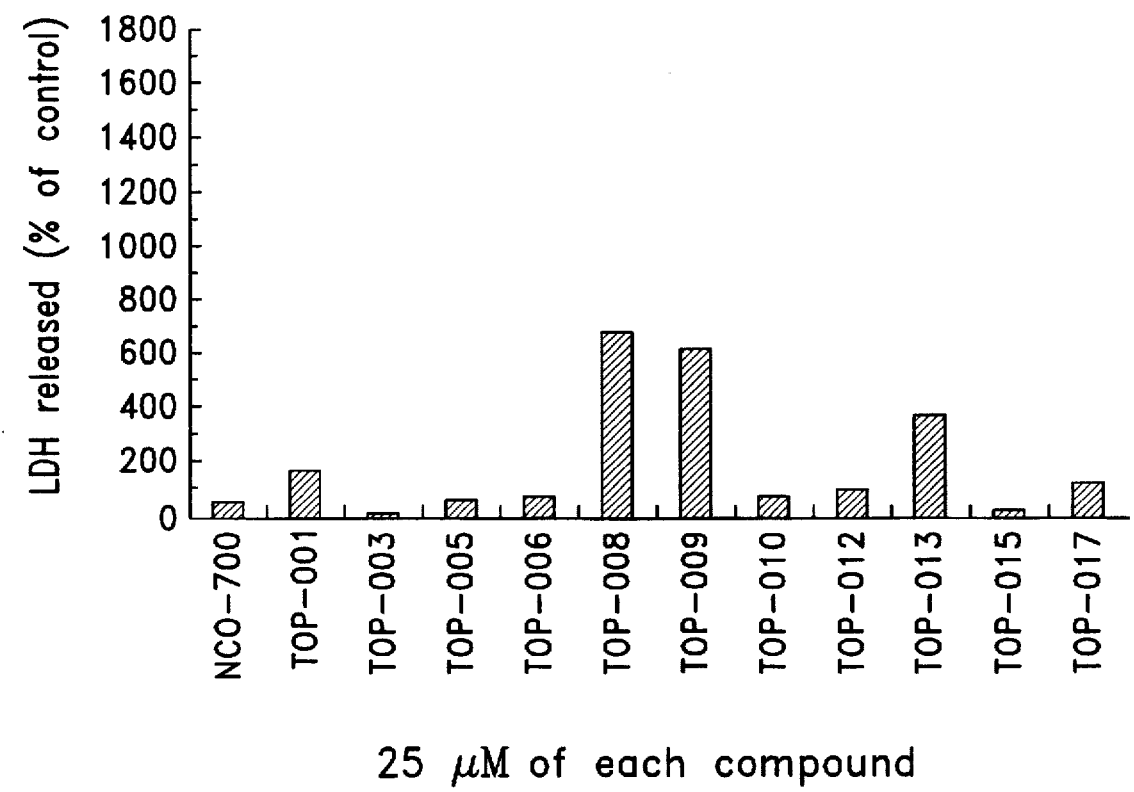
FIG. 25 is a graph showing the LDH release stimulated by NCO-700, TOP-008, and analogs in cancer cell death assays of human cancer cell line LS-174T (colon) at a concentration of 25 µM.
Figure 26:
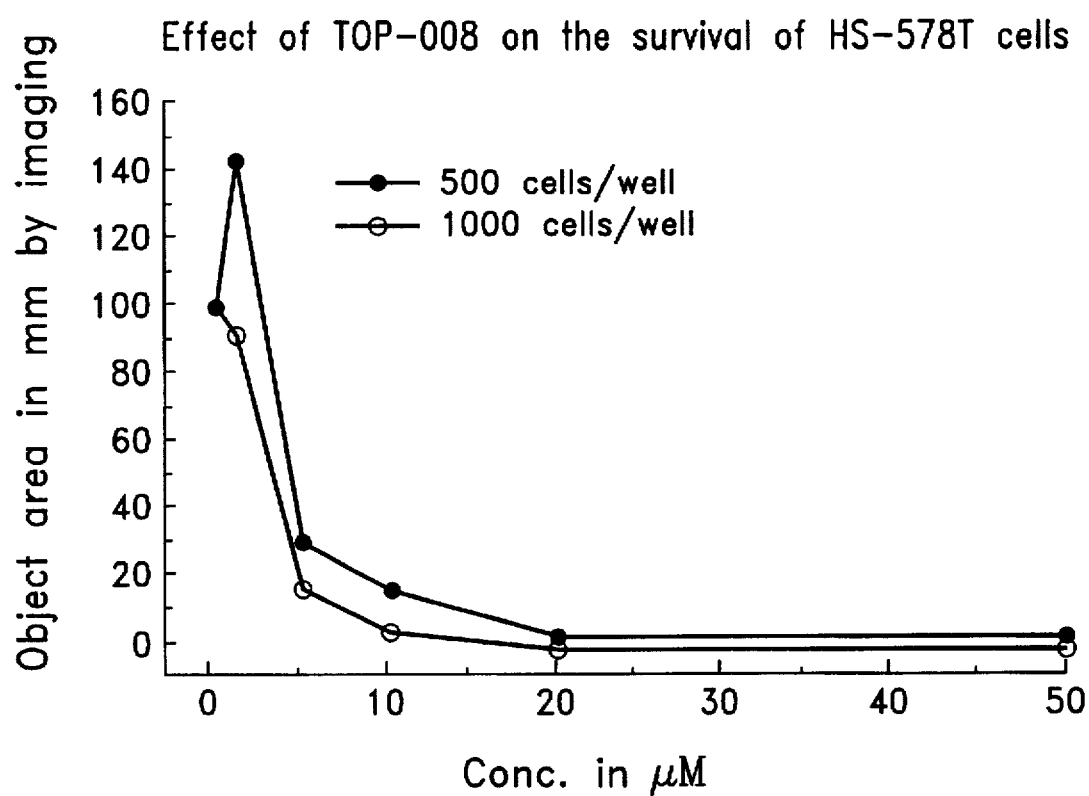
FIG. 26 is a graph showing the relationship between the object area and the concentration of TOP-008 in cancer cell survival assays of human cancer cell line HS-578T (breast) of 500 cells/well and 1,000 cells/well.
Figure 27:
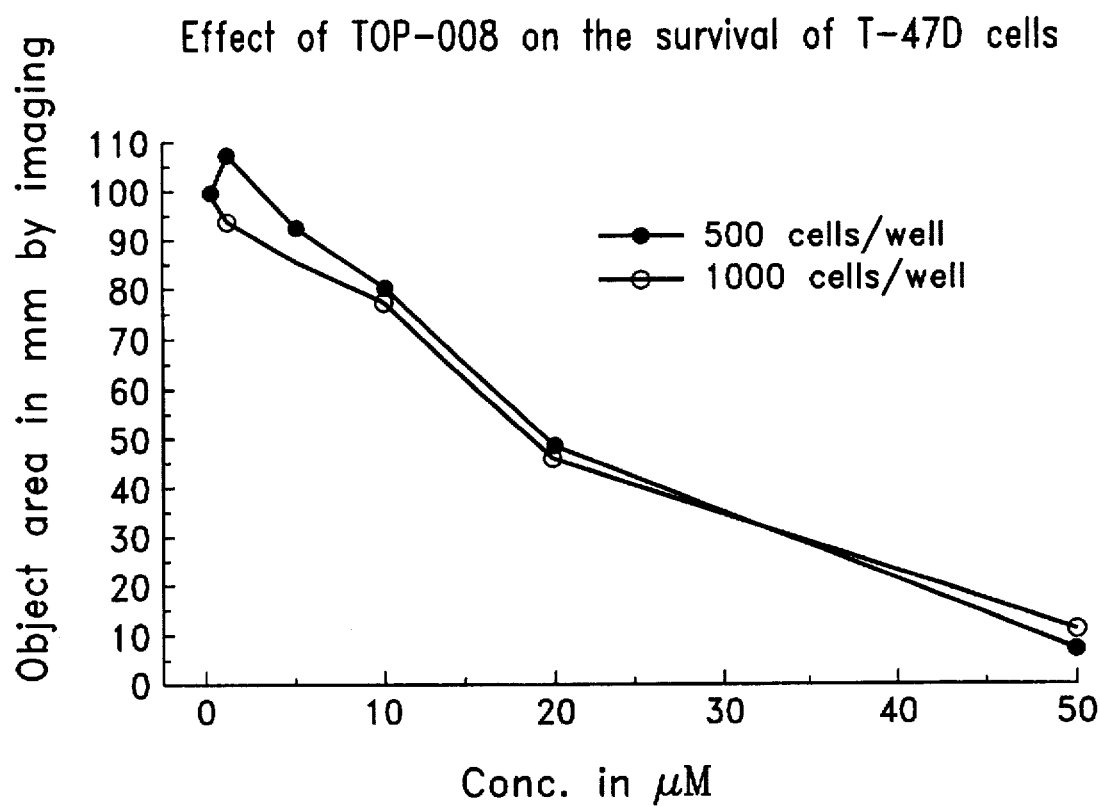
FIG. 27 is a graph showing the relationship between the object area and the concentration of TOP-008 in cancer cell survival assays of human cancer cell line T-47D (breast) of 500 cells/well and 1,000 cells/well.
Figure 28:
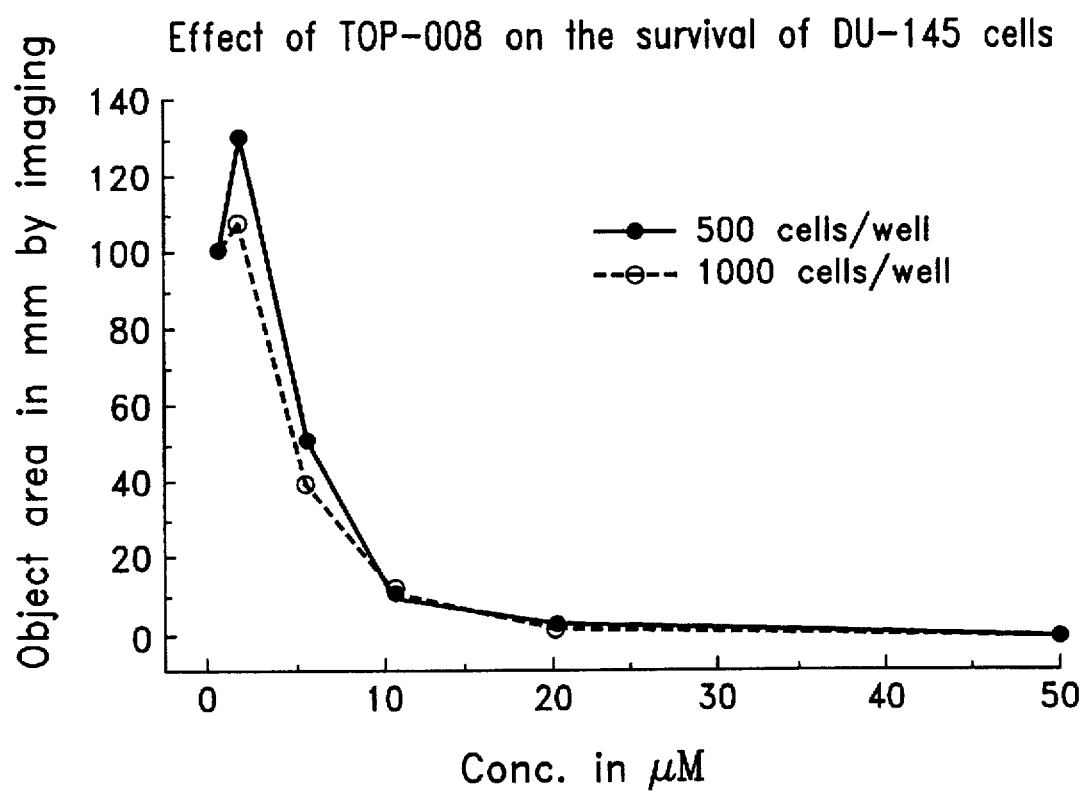
FIG. 28 is a graph showing the relationship between the object area and the concentration of TOP-008 in cancer cell survival assays of human cancer cell line DU-145 (prostate) of 500 cells/well and 1,000 cells/well.
Figure 29:
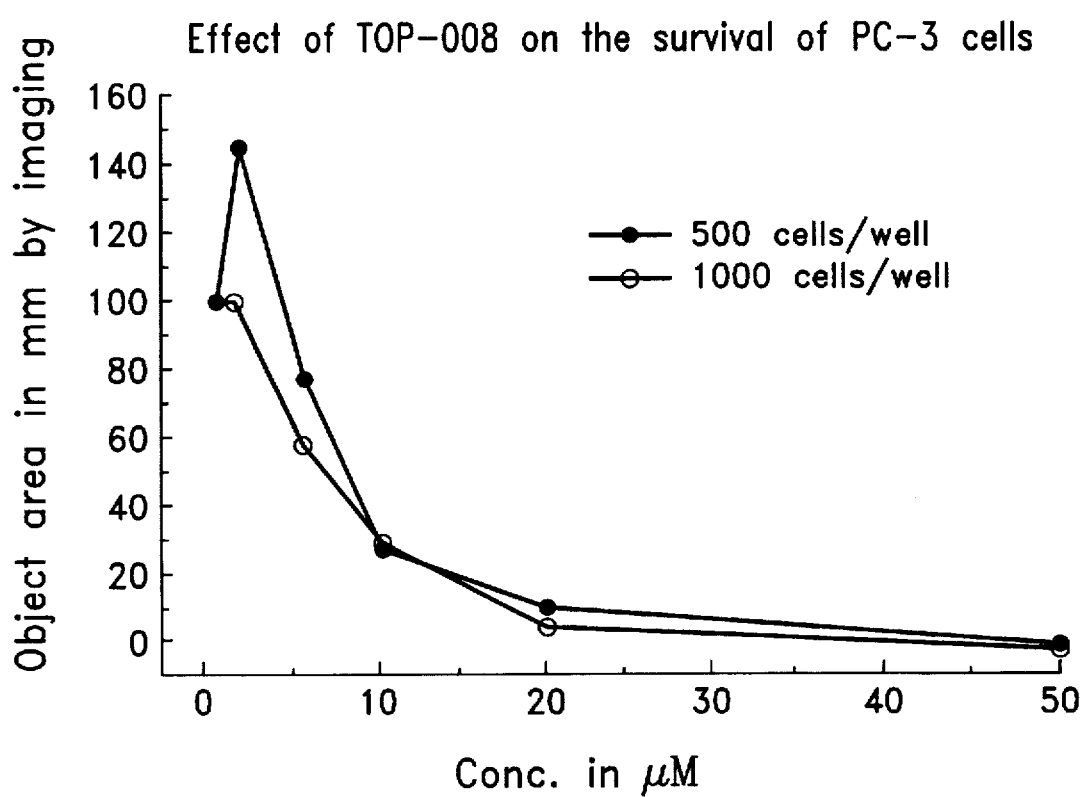
FIG. 29 is a graph showing the relationship between the object area and the concentration of TOP-008 in cancer cell survival assays of human cancer cell line PC-3 (prostate) of 500 cells/well and 1,000 cells/well.
Figure 30:
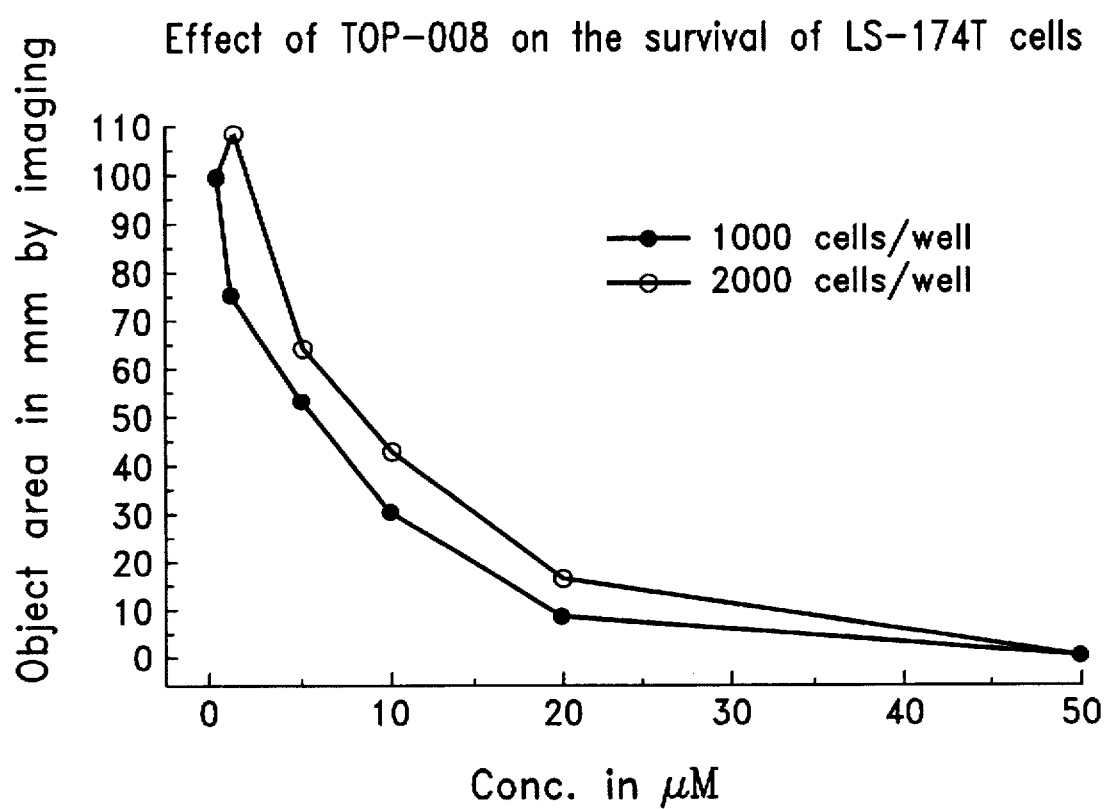
FIG. 30 is a graph showing the relationship between the object area and the concentration of TOP-008 in cancer cell survival assays of human cancer cell line LS-174T (colon) of 1,000 cells/well and 2,000 cells/well.
Figure 31:
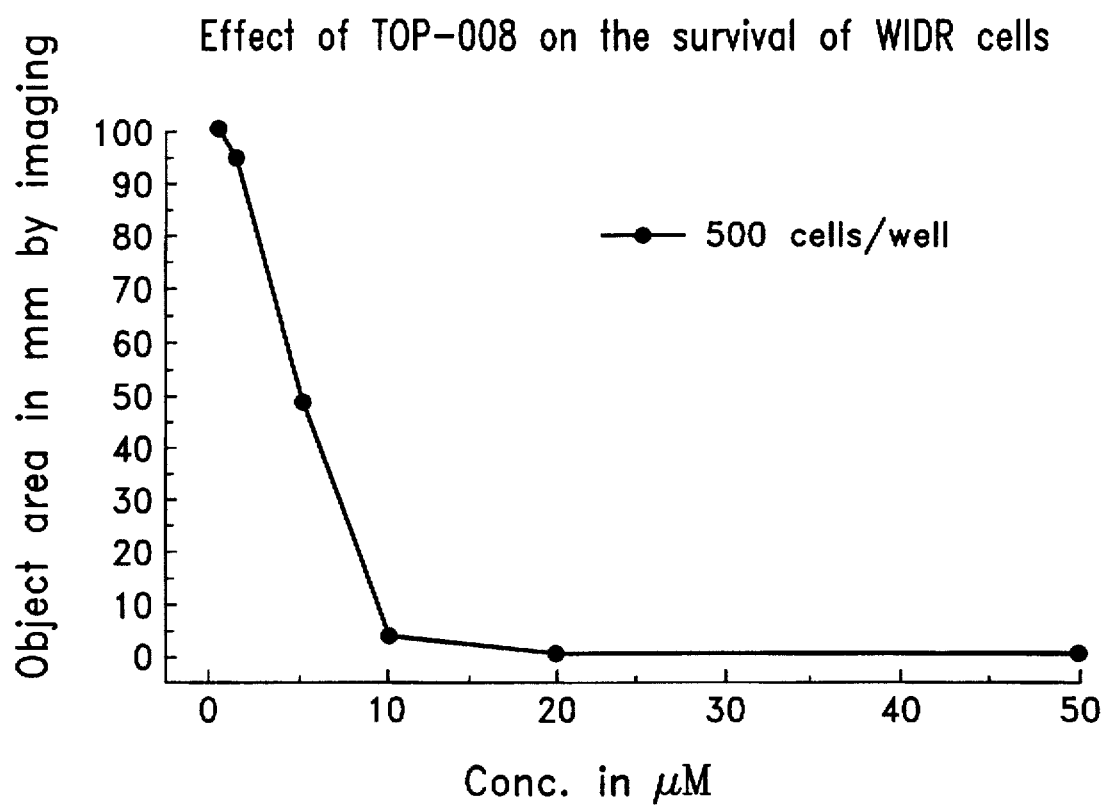
FIG. 31 is a graph showing the relationship between the object area and the concentration of TOP-008 in cancer cell survival assays of human cancer cell line WIDR (colon) of 500 cells/well.

6) NCO-700 Effect on Human Colon Cancer Cells Grown In Vivo in the SRC Assay: The effect of NCO-700 on a colon cancer line was tested in the SRC assay. Three groups of animals (n=18 total) were tested with two concentrations of NCO-700 including 50 mg/kg and 100 mg/kg. As shown in FIG. 19, there is a dose response effect of NCO-700 in decreasing the size of the tumor in the mice. Whereas the 50 mg/kg had slight effect, there was a significant anti-neoplastic effect of NCO-700 at the 100 mg/kg level. These studies confirm the high potential of NCO-700 and related compounds as new anti-neoplastic agents.

Conclusion

Experiment 1 establishes that NCO-700, alone, is highly effective as an anti-neoplastic agent versus selective tumors. The NCO-700 analog, TOP-008, was three-fold more potent than NCO-700 in terms of anti-neoplastic potency. The mechanism of NCO-700's anti-neoplastic activity appears to be based on an apoptosis-related mechanism.

EXPERIMENT 2

Anti-neoplastic Activity of TOP-008 and Other NCO-700 Analogs Alone

TOP-001 Bis[benzyl (2R,3R)-3-[(S)-3-methyl-1-[4-(2,3,4-trimethoxyphenylmethyl) piperazin-1-ylcarbonyl]butylcarbamoyl]oxirane-2-carboxylate] sulfate

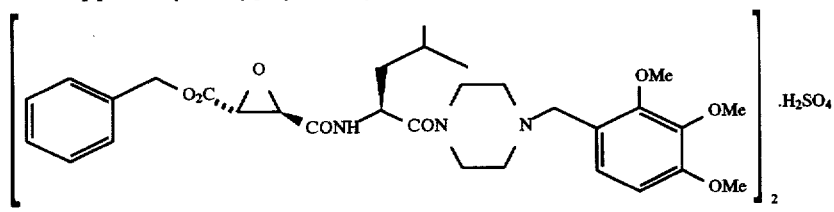

TOP-003 Bis[trimethylacetoxymethyl (2R,3R)-3-[(S)-3-methyl-1-[4-(2,3,4-trimethoxy phenylmethyl)piperazin-1-ylcarbonyl]butylcarbamoyl]oxirane-2-carboxylate] sulfate

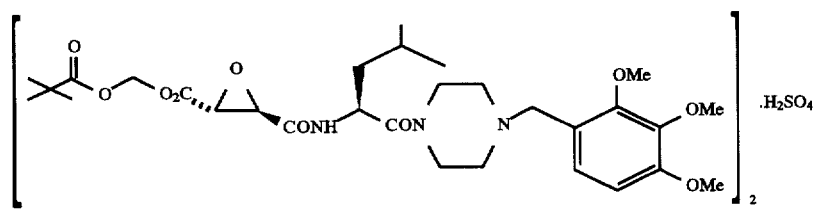

TOP-005 Bis[phenyl (2R,3R)-3-[(S)-3-methyl-1-[4-(2,3,4-trimethoxyphenylmethyl) piperazin-1-ylcarbonyl]butylcarbamoyl]oxirane-2-carboxylate]sulfate

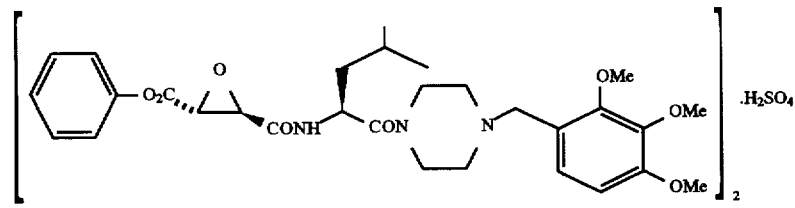

TOP-006 Bis[5-indanyl (2R,3R)-3-[(S)-3-methyl-1-[4-(2,3,4-trimethyoxyphenylmethyl) piperazin-1-ylcarbonyl]butylcarbamoyl]oxirane-2-carboxylate]sulfate

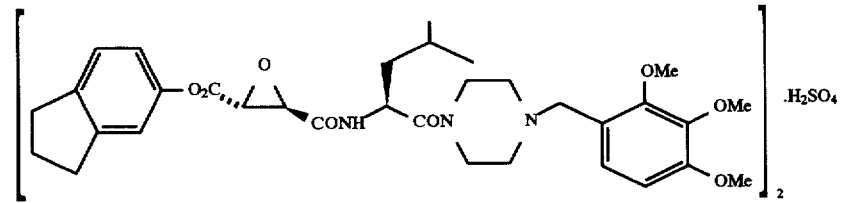

TOP-010 Bis[2-(2,5-dioxo-1-pyrrolidinyl)ethyl (2R,3R)-3-[(S)-3-methyl-1-[4-(3-phenyl-2-propenyl)piperazin-1-ylcarbonyl]butylcarbamoyl]oxirane-2-carboxylate]sulfate

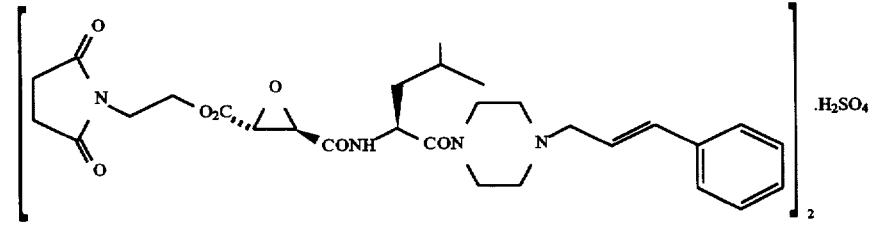

TOP-012 Bis[3-oxo-2-benzoxolan-1-yl (2R,3R)-3-[(S)-3-methyl-1-[4-(3-phenyl-2-propenyl)piperazin-1-yl carbonyl]butylcarbamoyl]oxirane-2-carboxylate]sulfate

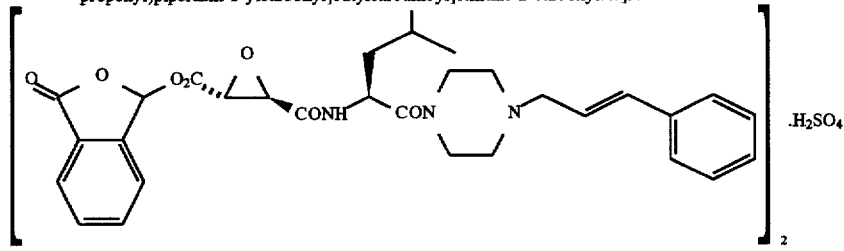

TOP-015 Bis[(2R,3R)-2-benzylcarbamoyl-3-[(S)-3-methyl-1-[4-(2,3,4-trimethoxyphenyl methyl)piperazin-1-ylcarbonyl]butylcarbamoyl]oxirane]sulfate

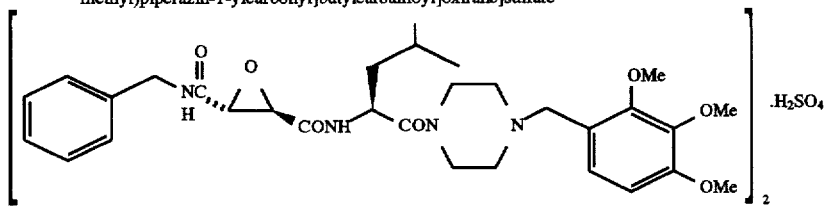

Methods

As described in Experiment I, three different assays were performed to measure anti-neoplastic activity of compounds.

Results

1) NCO-700 Analogs and Cancer Cell Death: The first assays performed measured the anti-neoplastic activity of NCO-700 analogs in cell death assays against a number of human cancer cells. The results of these experiments are shown in FIGS. 20–25, where a bar graph indicates the activity of a particular analog as measured by the % LDH released, with higher values of LDH released indicating greater anti-neoplastic activity (apoptosis). All analogs were tested at a concentration of 25 µM. From these assays, it can be seen that analogs of NCO-700 are highly selective in their anti-neoplastic activity, with some analogs showing significantly greater activity than NCO-700 itself. The analogs will have significant anti-neoplastic activities when used in conjunction with standard chemotherapeutic agents on drug-resistant tumors, even when the analogs are not significantly effective in apoptosis of the tumors.

2) TOP-008 and Cancer Cell Survival Assay: FIGS. 26–31 show the effect of increasing the dose of TOP-008 against a number of cancer cell lines. The survival studies confirm that TOP-008 is a highly active anti-neoplastic agent (apoptosis agent) and in some cases is much more active than NCO-700. For example, if the activity of NCO-700 and TOP-008 are compared against the human colon cancer cell line WIDR (FIG. 16 in Experiment 1 versus FIG. 31) it is seen that the effective dose of TOP-008 is much lower in this particular assay.

EXPERIMENT 3

Anti-neoplastic Activity of NCO-700 and Related Analogs Alone on Pancreatic Cancer Cells Methods As described in Experiment 1, the cancer cell death assays were performed to measure anti-neoplastic activity of the compounds, NCO-700, TOP-001, TOP-003, TOP-005, TOP-006, TOP-008, TOP-009, TOP-010, TOP-012, TOP-013, TOP-015, and TOP-017.

Cell Lines Utilized

The following cell lines were obtained from the American Type Tissue Culture Laboratory and cultured according to their specifications: Human pancreatic cancer cell lines ASPC-1 and HS-766T.

Results

Figure 32:
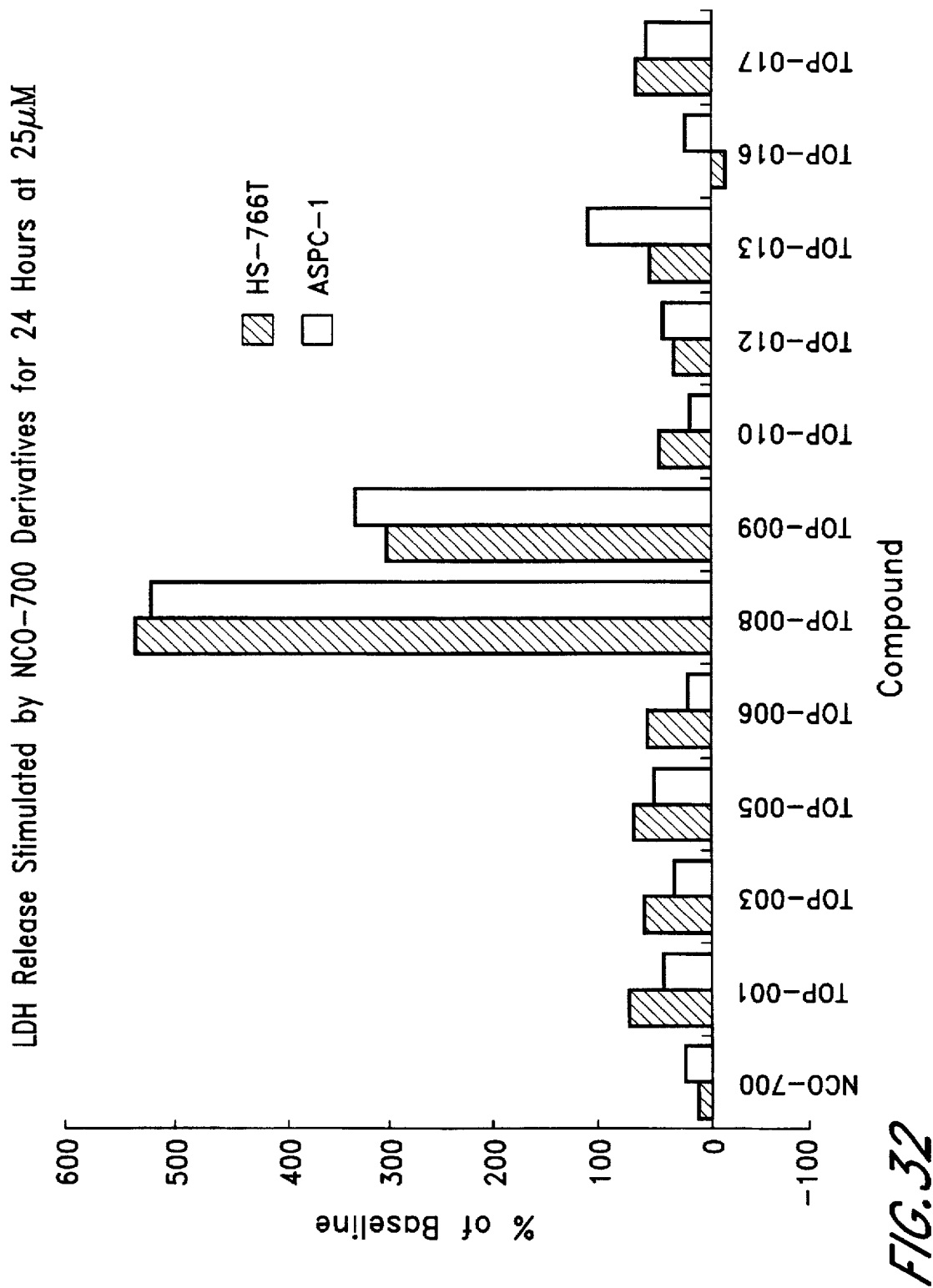
FIG. 32 is a graph showing the LDH release stimulated by NCO-700, TOP-008, and analogs in cancer cell death assays of human cancer cell lines HS-766T (pancreas) and ASPC-1 (pancreas) at a concentration of 25 μM.

The results of the experiments are shown in FIG. 32, where a bar graph indicates the activity of a particular analog as measured by the % LDH release stimulated by each analog for 24 hours, with higher values of LDH released indicating greater anti-neoplastic activity (apoptosis). All analogs were tested at a concentration of 25 µM. From these assays, it can be seen that some analogs, especially TOP-008 and TOP-009, show significantly greater activity than NCO-700 itself.

EXPERIMENT 4

Comparison of NCO-700 and Calpain Inhibitor in Cancer Cell Death Assay

Figure 33:
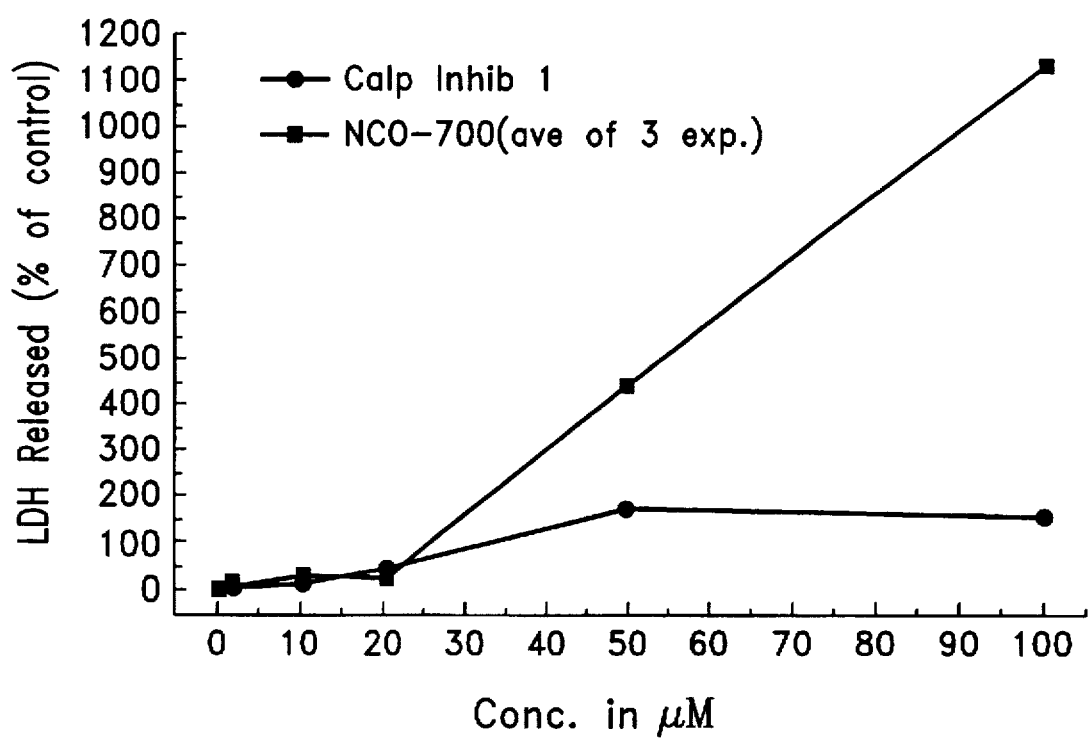
FIG. 33 is a graph showing the relationship between LDH released and the concentration of NCO-700 and Calpain inhibitor 1 in cancer cell death assays of human cancer cell line DU-145 (prostate).

Based on Experiment 1 above, the anti-cancer activity of NCO-700 and Calpain inhibitor 1 (N-acetyl-leu-leu-norleucinal, $C_{20}H_{37}N_3O_4$) was tested in cancer cell death assays of human cancer cell line DU-145. FIG. 33 shows data with calpain inhibitor 1 obtained from Boehringer-Ingelheim, and NCO-700. In FIG. 33, NCO-700 is clearly superior to the other inhibitor. At a concentration of 100 µM, NCO-700 is almost 10-fold more potent.

When an attempt of testing Calpain Inhibitor 1 in long-term assays (cell survival assay) was made, it was toxic to the cells, as would be expected from its chemical structure, and the toxicity of Calpain Inhibitor 1 would interfere with testing this compound in cell survival assays or in vivo.

EXPERIMENT 5

Anti-neoplastic Activity of NCO-700, TOP-008, and Related Analogs Alone

TOP-201 Sodium (2RS,3RS)-3-[(S)-3-methyl-1-(4-phenylmethyl)piperazin-1-
ylcarbonyl]butylcarbamoyl]oxirane-2-carboxylate

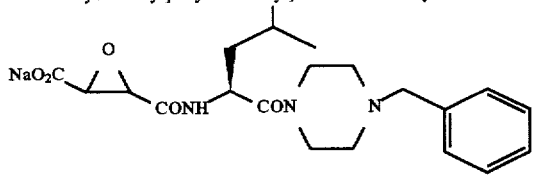

TOP-202 Sodium (2RS,3RS)-3-[(S)-3-methyl-1-[4-(4-methoxyphenylmethyl)piperazin-1-
ylcarbonyl[butylcarbamoyl]oxirane-2-carboxylate

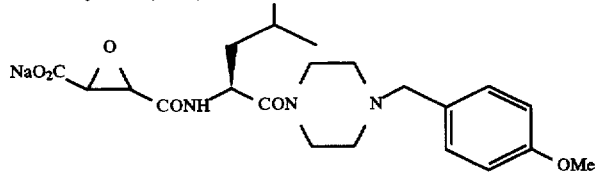

TOP-203 Sodium (2R,3R)-3-[(S)-3-methyl-1-[4-(2-pyrimidinyl)piperazin-1-
ylcarbonyl]butylcarbamoyl]oxirane-2-carboxylate

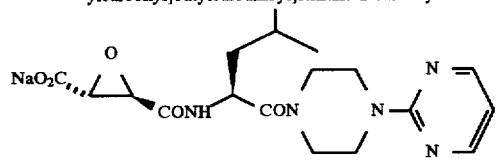

TOP-204 Sodium (2S,3S)-3-[(S)-3-methyl-1-[4-(2-pyrimidinyl)piperazin-1-
ylcarbonyl]butylcarbamoyl]oxirane-2-carboxylate

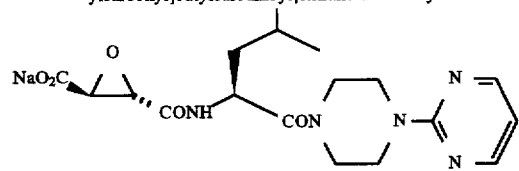

TOP-205 Bis[ethyl (2RS,3RS)-3-[(S)-3-methyl-1-[4-(2,3,4-trimethoxyphenylmethyl)
piperazin-1-ylcarbonyl]butylcarbamoyl]oxirane-2-carboxylate]sulfate

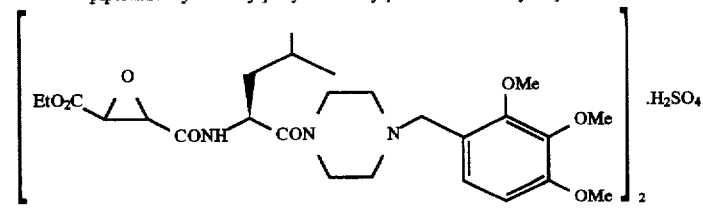

TOP-206 Bis[isobutyl (2RS,3RS)-3-[(S)-3-methyl-1-[4-(2,3,4-trimethoxyphenyl
methyl)piperazin-1-ylcarbonyl]butylcarbamoyl]oxirane-2-carboxylate]sulfate

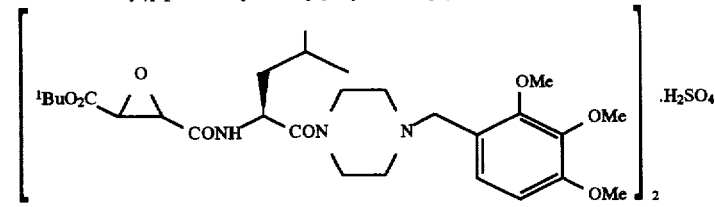

TOP-207 Potassium (2R,3R)-3-[(S)-3-methyl-1-[4-(2,3,4-trimethoxyphenylmethyl)
piperazin-1-ylcarbonyl]butylcarbamoyl]oxirane-2-carboxylate

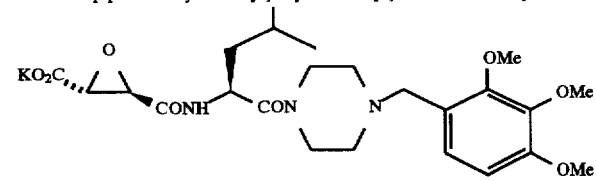

TOP-007 Sodium (2R,3R)-3-[(S)-3-methyl-1-[4-(3-phenyl-2-propenyl)piperazin-1-ylcarbonyl]butylcarbamoyl]oxirane-2-carboxylate

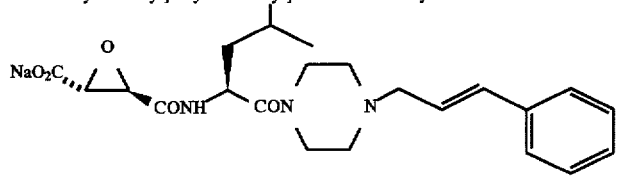

Figure 34:
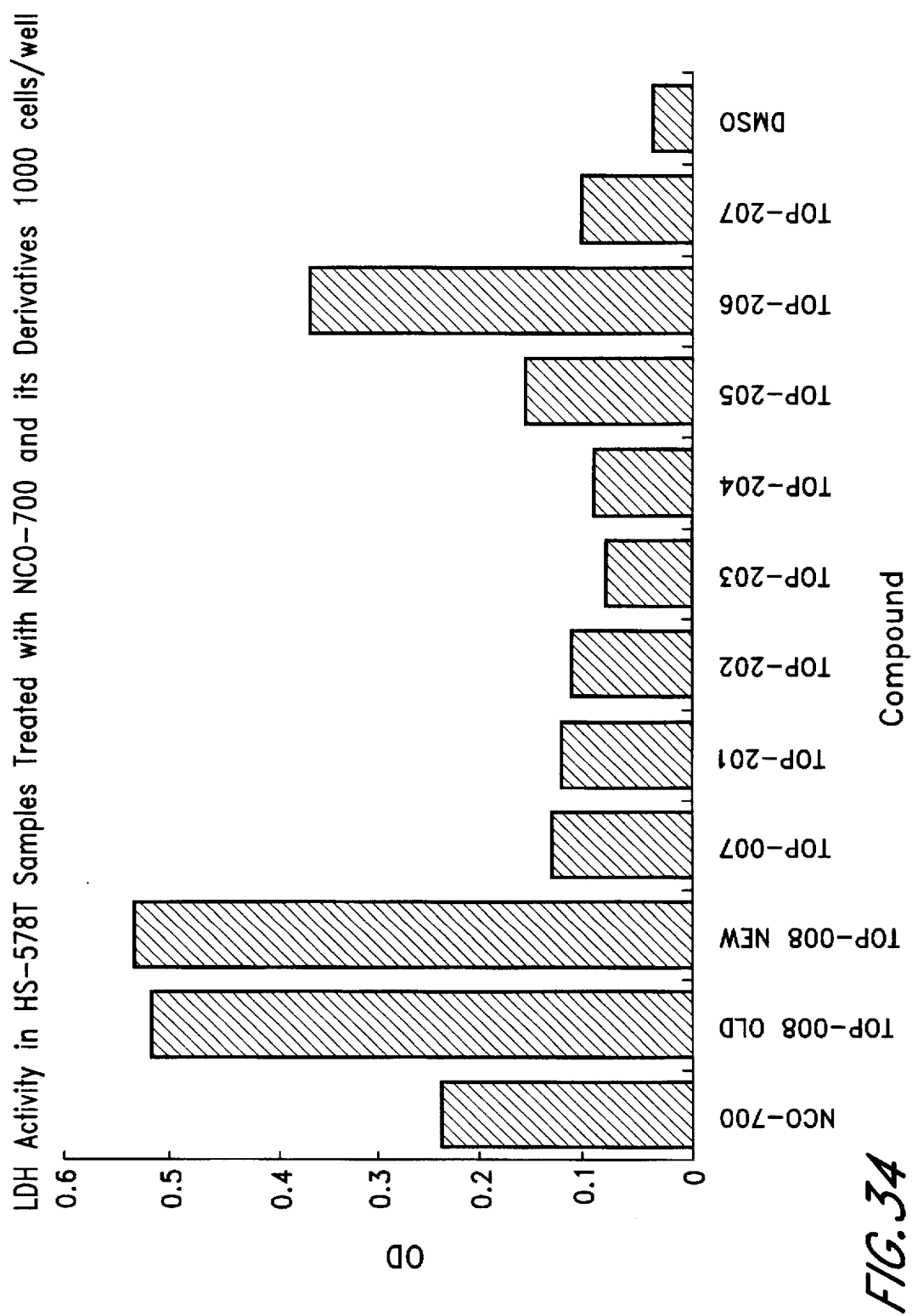
FIG. 34 is a graph showing the LDH release stimulated by NCO-700, TOP-008, and analogs in cancer cell death assays of human cancer cell line HS-578T (1,000 cells/well).
Figure 35:
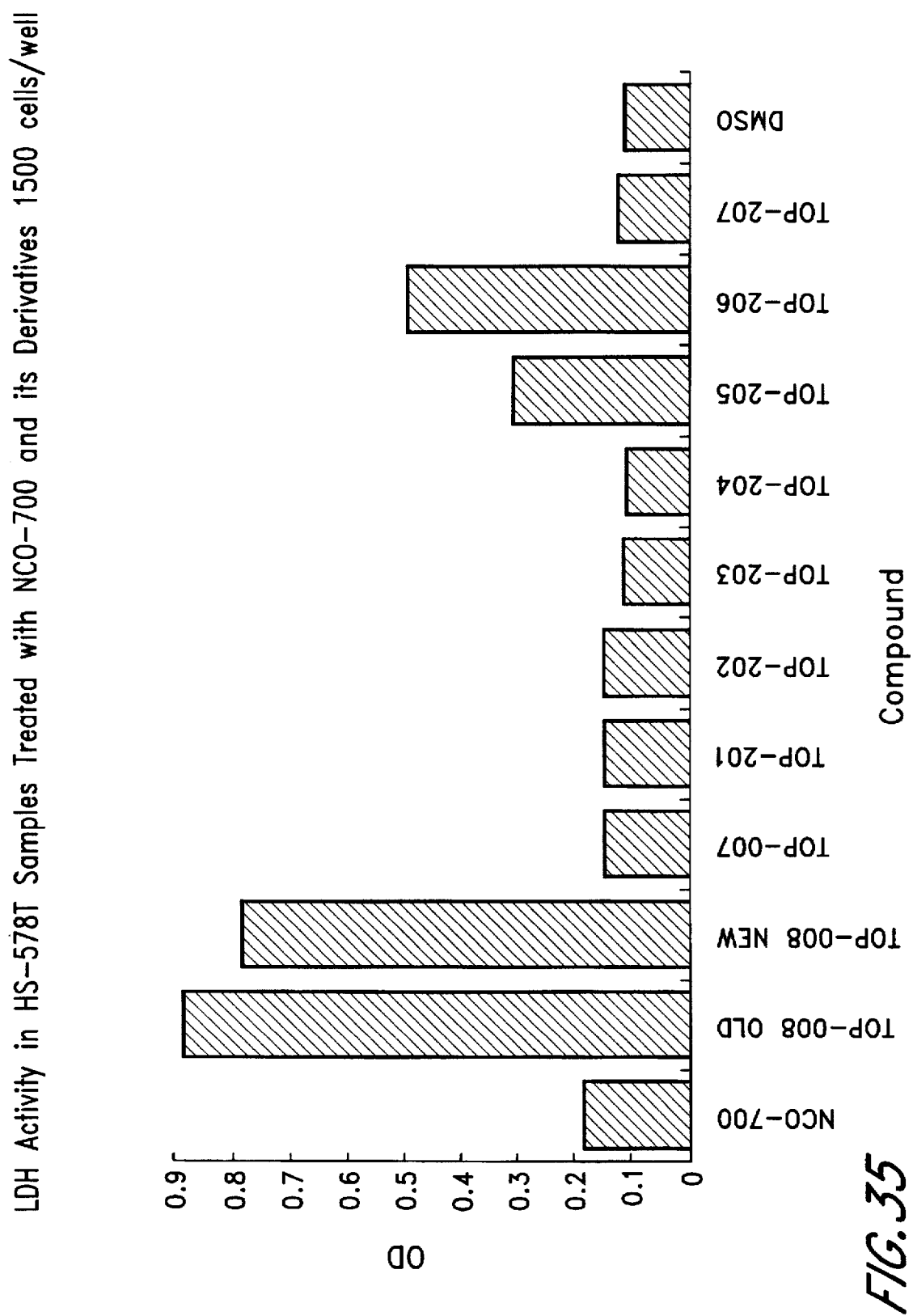
FIG. 35 is a graph showing the LDH release stimulated by NCO-700, TOP-008, and analogs in cancer cell death assays of human cancer cell line HS-578T (1,500 cells/well).

Based on Experiment 1 above, the anti-cancer activity of NCO-700, TOP-008, and analogs, TOP-201, 202, 203, 204, 205, 206, 207, and 007, was tested in cancer cell death assays of human cancer cell line HS-578T. In FIGS. 34 (1,000 cells/well) and 35 (1,500 cells/well), a bar graph indicates the activity of a particular analog as measured by the % LDH released (DMSO, dimethyl sulfoxide=control), with higher values of LDH released indicating greater anti-neoplastic activity. All analogs were tested at a concentration of 25 μM. From these assays it can be seen that TOP-008 (six month old (OLD) and newly synthesized (NEW)) had very good anti-neoplastic activity, and TOP-206 and NCO-700 had fairly good anti-neoplastic activity. The other analogs tested also showed some anti-cancer activity. Sulfate forms appear to exhibit better results.

EXPERIMENT 6

Anti-Neoplastic Activity of TOP-008 in Apoptosis Detection Assay

Figure 36A:
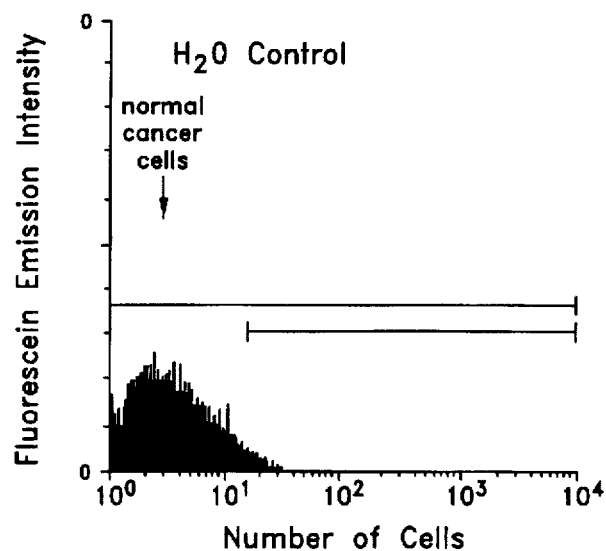
FIGS. 36a, 36b, and 36c indicate normal cancer cells, cancer cells with TOP-008 (50 μM), and cancer cells with TOP-008 (25 μM), respectively.
Figure 36B:
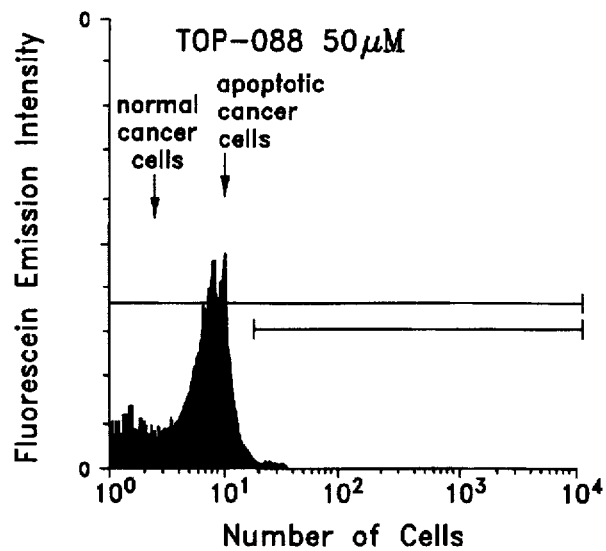
Figure 36C:
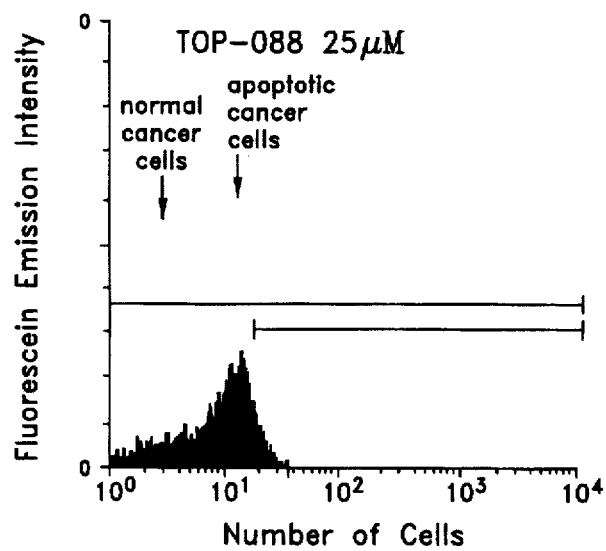

Anti-neoplastic activity of TOP-008 was tested using a commercially available kit, Apoptosis Detection Kit, from R & D SYSTEMS (Minnesota) in which annexin V, a member of the calcum and phospholipid binding proteins, is used to detect apoptosis, following the protocol recommended by the manufacturer. TOP-008 was tested at a concentration of 50 μM, using Human breast cancer cell line HS-578T. Cells were washed in cold PBS twice and resuspended in a small volume of 1× binding buffer. Fluorescein-labeled annexin V and propidium iodide were added to the cells. The cells expressing phosphatidylserine on the outer leaflet of cell membranes bind annexin V and cells with a compromised cell membrane allow propidium iodide to bind to the cellular DNA. The resulting cells when immediately analyzed by flow cytometry can present three potential populations of cells: live cells which will not stain with either fluorochrome, necrotic cells which will stain with both fluorochrome, and cells undergoing apoptosis which will stain only with the annexin V-FITC reagent. Analysis was performed on cytometers equipped with a single laser emitting excitation light at 488 nm. The annexin V-FITC-generated signal was detected in the FITC signal detector (FL1). The results are shown in FIG. 36 in which the vertical axis is the intensity of fluorescein emission, and the horizontal axis is the number of cells. FIG. 36a, 36b, and 36c show normal cancer cells (control), cancer cells with TOP-008 (50 μM), and cancer cells with TOP-008 (25 μM), respectively. FIG. 36 clearly shows that TOP-008 induced apoptosis in human breast cancer cells.

EXPERIMENT 7

Apoptosis Induced DNA Fragmentation

PC-3, a prostate tumor cell line, was treated with 25 μM TOP-008, 50 μM NCO-700, or water for 48 hours. The DNA from each sample was purified by phenol extraction, and the fragmentation was resolved on an agarose gel. As a result, both samples treated with TOP-008 and NCO-700 showed significant DNA fragmentation while the control (treated with water) did not. This fragmentation has been shown to be an indication of apoptosis (Jarvis et al., Canc. Res. 1154:1707–1714, 1994, Pandey et al., Biochem. Cell Biol. 72:625–629, 1994).

The foregoing experiments have established the new aspect of the piperazine derivatives of the present invention, apoptosis, i.e., the derivatives are highly effective alone as an anti-neoplastic agent. The following experiment is an example which shows that the piperazine derivatives have significant anti-neoplastic activities when used in conjunction with standard chemotherapeutic agents such as vinblastine and adriamycin on drug-resistant tumors, even when the compounds are not significantly effective in apoptosis of certain cancer lines.

EXPERIMENT 8

Multidrug Resistance-Reversing Effect of NCO-700 in Human Neoplasms

Methods and Results

In this Experiment, four different assays were utilized to measure the ability of NCO-700 to block or reverse the drug-resistant phenotype of cancer cells or tumors. These assays include:

1. Drug Accumulation Assays, where the effect of NCO-700 on the uptake of radioactive ($^3$H)-vinblastine, an anticancer drug, is measured in cultured cancer cells, that are both drug-resistant and drug-sensitive (Reference 3).
2. Cell Survival Assays, where the effect of NCO-700 to enhance cancer cell killing by vinblastine was measured.
3. In Vivo Model of Tumorigenicity, where the effect of NCO-700 in the ability of adriamycin to reduce tumor mass in drug-resistant neoplasms was measured.
4. Human Tumor Biopsy Assays, where the effect of NCO-700 to enhance killing, by either vinblastine or adriamycin, of cancer cells cultured directly from patient's tumors (Von Hoff et al., Cancer Res. 43:1926–1931, 1983).

Cell Lines Utilized

In the first two in vitro assays, the drug accumulation assay and the cell survival assay, a human pharyngeal carcinoma cell line (KB-V-1) which is highly resistant to anticancer drugs was used. This cell line was developed by Drs. Ira Pastan and Michael Gottesman of the National Cancer Institute, by step-wise selection in colchicine of drug-resistant cells. The control cancer cell line (KB-3), from which the resistant cell lines were derived, is sensitive to anticancer drugs. The resistant KB-V-1 cell line is approximately 275 times more resistant to vinblastine than the sensitive KB-3 line and has a greatly amplified mdr gene which generates the observed resistance.

For the in vivo model of tumorigenicity, cell lines developed by Pastan and Gottesman which can grow as solid tumors in nude mice were utilized. This cell line was designated KB-CH 8-5, and was a nonreverting resistant cell line. All of these cancer cell lines were generously provided by Dr. Gottesman.

For the tumor biopsy assay, primary cell cultures were propagated directly from tumor specimens removed from patients. The cells were grown in suspension culture, treated with adriamycin or vinblastine plus NCO-700, and plated onto soft agar and incubated for two weeks before cell survival was determined.

Table 2 below summarizes results obtained in the drug accumulation assay. Measurement of [$^3$H]-vinblastine accumulation was performed by the methods developed in the laboratory of Drs. Gottesman and Pastan (Fojo et al., *Cancer Res.* 45:3002–3007, 1985). In this method, KB-V-1 and KB-3 cells were plated in 10% fetal bovine serum at a density of $3 \times 10^5$ cells per well in 24-well Costar plates. The next day, the growth medium was replaced with Dulbecco's modified Eagle's medium with or without (control cells) 20 µM NCO-700. After ten minutes, the medium was removed and replaced with assay medium (0.5 ml) containing 0.1 µCi, (13 pmol) [$^3$H]-vinblastine in the presence or absence of 20 µM NCO-700. After an additional 30 min, the medium was removed, the plates were washed three times in ice-cold phosphate-buffered saline, the cells were detached with trypsin, and radioactivity determined by scintillation counting.

TABLE 2

NCO-700 STIMULATES THE ACCUMULATION OF VINBLASTINE IN RESISTANT HUMAN CANCER CELLS DRUG ACCUMULATION (pmole vinblastine/mg protein)

|  | KB-V-1 (resistant cells) | KB-3 (sensitive cells) |
| --- | --- | --- |
| CONTROL (vinblastine alone) | 0.29 ± 0.03 | 2.99 ± 0.12 |
| 20 µM NCO-700 + vinblastine | 1.56 ± 0.03 | 3.17 ± 0.09 |

As shown in Table 2 above, the accumulation of the anticancer drug, vinblastine, was severely restricted in the drug-resistant cell line, KB-1, due to the action of the mdr pump. However, when this cell line was exposed to 20 µM NCO-700, there was a 5-fold increase in the amount of vinblastine that remained in the cancer cell. As shown in Table 3 below, this leads to an enhanced killing of the drug-resistant cells.

TABLE 3

NCO-700 INCREASES THE KILLING OF RESISTANT CANCER CELLS BY VINBLASTINE

| CELL LINE | VINBLASTINE (ng) to kill 50% of cells |
| --- | --- |
| KB-3 (sensitive) | 3.2 |
| + 25 µM NCO-700 | 1.6 |
| KB-V-1 (resistant) | 792 |
| + 25 µM NCO-700 | 148 |

The cell survival experiments shown above were performed by plating KB-3 (sensitive) and KB-V-1 (resistant) cells in 32 mm well plastic dishes at a cell density of 300–500 cells per well. Vinblastine and NCO-700 were added 16 hours after the initial cell plating. After 10 days of incubation at 37°, cell colonies were stained and counted.

As shown in Table 3, there was a dramatic effect of NCO-700 on the survival of KB-V-1 resistant cancer cells. The levels of vinblastine needed to kill 50% of the tumor cells dropped from 825 ng to 160 ng of vinblastine when the resistant cells were co-incubated with 30 µM NCO-700. This effect reflects inhibition or blocking of the mdr pump, resulting in increased levels of anticancer drug in the cell. Interestingly, in this Experiment, there was also a slight enhancement of the killing of sensitive KB-3 cells as well.

Figure 37:
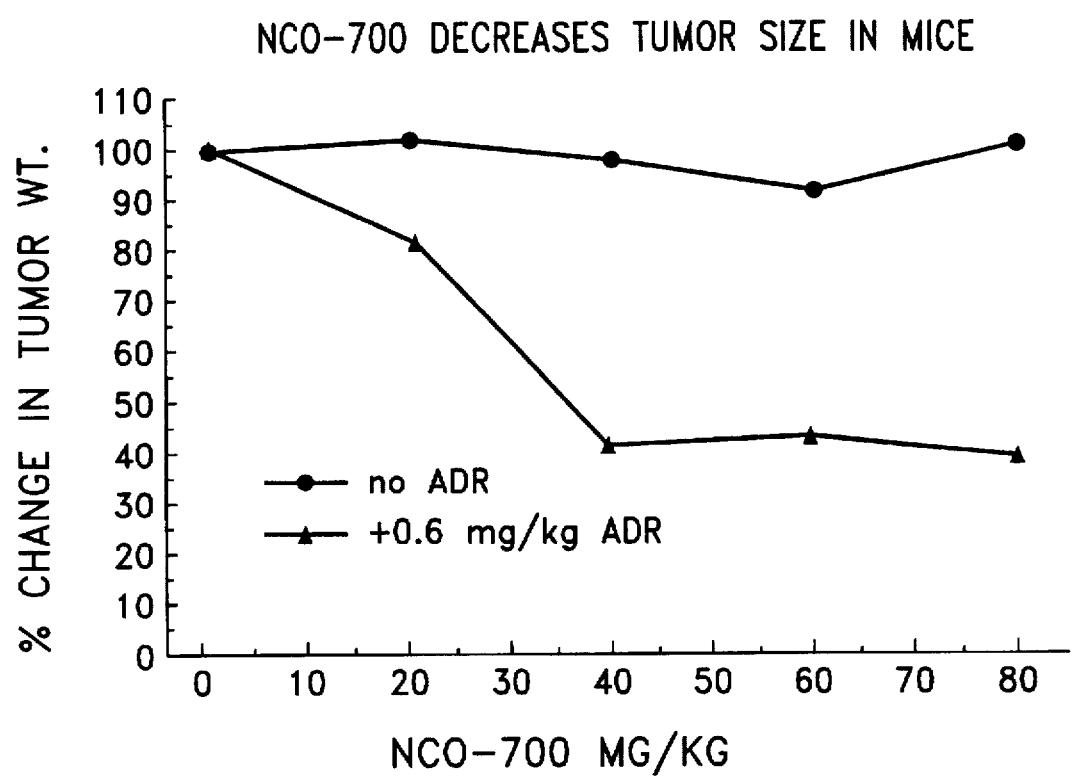
FIG. 37 is a graph showing the relationship between changes in tumor weight and the dosage of NCO-700 in nude mice treated with adriamycin and without adriamycin.

In the next series of experiments, an in vivo model of tumorigenicity was utilized to examine the effect of NCO-700 on tumor mass. These experiments were performed with the cell line KB-CH-8/5, which is a cell line developed by Drs. Gottesman and Pastan, specifically for use in animals as the cells from solid tumors in vivo. Nude male mice, 5–6 weeks old and weighing between 25–30 g, were injected subcutaneously with $2-5 \times 10^6$ KB-CH-8/5 cells and treated for 14 days with 0.6 mg/kg adriamycin and with or without NCO-700 in doses ranging from 0–80 mg/kg NCO-700 per day. The data shown in FIG. 37 were obtained by weighing the well-encapsulated, excised tumor and recording the body weight of the mice. Clearly shown in FIG. 37, the addition of NCO-700 significantly potentiated the effect of adriamycin, especially at an amount of 40 mg/kg or more.

In a final series of experiments, the effect of NCO-700 on survival of cells cultured directly from biopsied patient tumors was performed. This technique, referred to as a human tumor cloning system, was developed by Von Hoff and associates (Von Hoff et al., *Cancer Res.* 43:1926–1931, 1983) and was used clinically to predict the course of chemotherapy for these patients. In this method, tumor biopsies were separated into cell suspensions and treated for 1 hour with either 0.4 mg/ml vinblastine (VLB) or 0.5 mg/ml adriamycin (ADR) plus or minus 20 µM NCO-700. The cell suspensions were washed after one hour of incubation and plated with soft agar. After 14 days of incubation at 37°, the percent of colonies surviving was scored. As a result, NCO-700 had significant activity in inhibiting the survival of certain human tumor cells. In two tumors tested from patients with breast cancer who were receiving chemotherapy, NCO-700 significantly sensitized these tumor cells to the actions of adriamycin (ADR) and vinblastine (VLB). In particular, the survival of tumor cells decreased to approximately ½ to ⅓ after exposure to NCO-700 and adriamycin. All other tumors tested showed varying degrees of positive response. Excellent responses were seen with a kidney tumor treated with NCO-700 and adriamycin, where the survival of the tumor cells decreased to approximately ¼ and with an ovarian tumor treated with NCO-700 and vinblastine where the survival decreased to approximately ⅓. The prediction on the mechanism of how NCO-700 is sensitizing these tumor cells to the anticancer drugs would be that NCO-700 is blocking or inhibiting the mdr pump from effluxing the cancer drug from the cell.

Conclusion

NCO-700 stimulated by 5-fold the accumulation of the anticancer drug, vinblastine, in human carcinoma cell lines. This resulted in a highly significant increase in the killing of these cancer cells. When NCO-700 was administered with adriamycin to nude mice carrying resistant human tumors (KB-CH 8-5), there was a decline, by 60%, of tumor mass without any corresponding loss of body weight, although NCO-700 was not significantly effective on its own. Finally, NCO-700 showed excellent activity in sensitizing to anticancer drugs, a number of primary tumor cell lines grown from patient biopsies.

The above experiment is an example which shows that the piperazine derivatives have significant anti-neoplastic activities when used in conjunction with standard chemotherapeutic agents such as vinblastine and adriamycin on drug-resistant tumors, even when the compounds are not significantly effective in apoptosis of certain cancer lines. Thus, as a clinical trial, first, a compound of the present piperazine derivatives is administered as a primary chemotherapeutic agent to a patient having cancer (irrespective of the existence of multidrug resistance), and when the compound does not appear to be effective on its own, another chemotherapy is additionally conducted as adjunctive therapy, e.g., the administration of other chemotherapeutic agents substantially contemporaneously with the present piperazine derivatives.

It will be understood by those of skill in the art that numerous variations and modifications can be made without departing from the spirit of the present invention. Therefore, it should be clearly understood that the forms of the present invention are illustrative only and are not intended to limit the scope of the present invention.

What is claimed is:

1. A method for inducing cell death in neoplastic cells, comprising:

administering a compound of formula I or a pharmaceutically acceptable salt thereof to a patient having neoplastic cells sensitive to said compound or said salt, in an amount sufficient to induce cell death in said neoplastic cells:

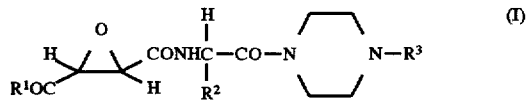

where
$R^1$ is hydroxyl or C1–4 alkoxyl,
$R^2$ is C3–4 alkyl, $R^3$ is C1–4 alkyl,

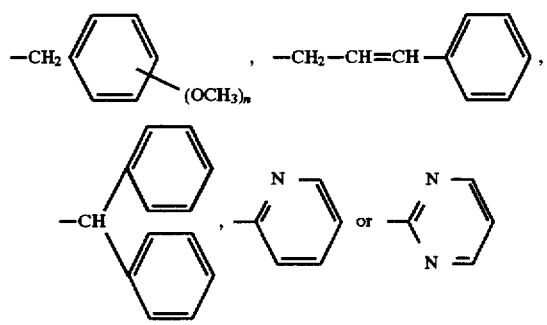

in which n is an integer of 0 to 3.

2. The method according to claim 1, wherein said compound is of the following formula:

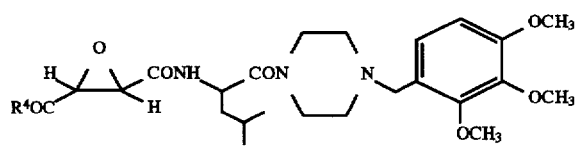

where $R^4$ is $C_2H_5O$—.

3. The method according to claim 1, wherein said compound is of the following formula:

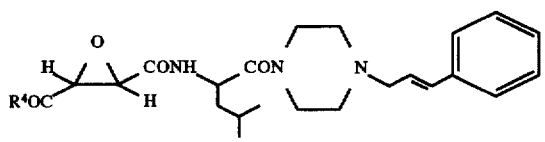

where $R^4$ is $C_2H_5O$—.

4. The method according to claim 1, wherein said compound is in the form of sulfate.

5. The method according to claim 1, wherein said neoplastic cells to be treated are selected from the group consisting of human breast cancer cells, human melanoma cells, human ovarian cancer cells, human colon cancer cells, human pancreatic cancer cells, and human prostate cancer cells.

6. The method according to claim 1, wherein said neoplastic cells to be treated are undifferentiated cancer cells.

7. The method according to claim 1, wherein said neoplastic cells to be treated carry an active mdr gene.

8. A method for treating neoplastic cells, consisting essentially of:

administering a compound of formula I or a pharmaceutically acceptable salt thereof to a patient having neoplastic cells sensitive to said compound or said salt, in an amount sufficient to induce cell death in said neoplastic cells:

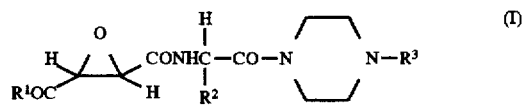

where
$R^1$ is hydroxyl or C1–4 alkoxyl,
$R^2$ is C3–4 alkyl, $R^3$ is C1–4 alkyl,

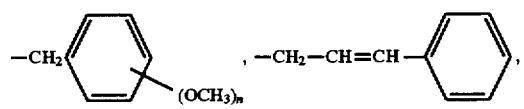

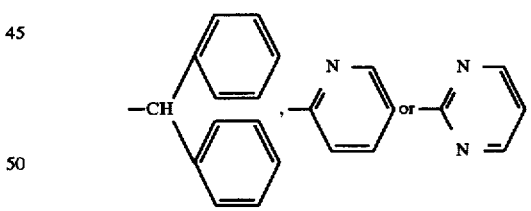

in which n is an integer of 0 to 3.

9. The method according to claim 8, wherein said compound is of the following formula:

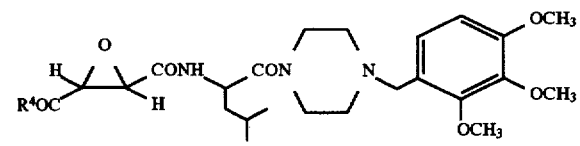

where $R^4$ is $C_2H_5O$—.

10. The method according to claim 8, wherein said compound is of the following formula:

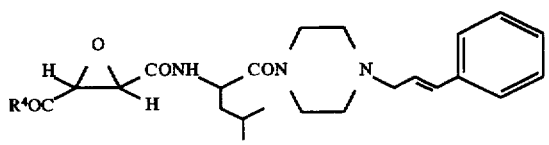

where $R^4$ is $C_2H_5O-$.

11. The method according to claim 8, wherein said compound is in the form of sulfate.

12. The method according to claim 8, wherein said neoplastic cells to be treated are selected from the group consisting of human breast cancer cells, human melanoma cells, human ovarian cancer cells, human colon cancer cells, human pancreatic cancer cells, and human prostate cancer cells.

13. The method according to claim 8, wherein said neoplastic cells to be treated are undifferentiated cancer cells.

14. The method according to claim 8, wherein said neoplastic cells to be treated carry an active mdr gene.

* * * * *